United States Patent
Karoor et al.

(10) Patent No.: US 8,066,658 B2
(45) Date of Patent: Nov. 29, 2011

(54) METHOD AND COMPOSITION FOR REMOVING UREMIC TOXINS IN DIALYSIS PROCESSES

(75) Inventors: Sujatha Karoor, Lake Bluff, IL (US); Brian Donovan, Chicago, IL (US); Ton That Hai, Mundelein, IL (US); Mari Katada, Evanston, IL (US); Luis Lu, Morton Grove, IL (US); Leo Martis, Long Grove, IL (US); Stavroula Morti, Evanston, IL (US); Salim Mujais, Northbrook, IL (US); Paul J. Sanders, Greendale, WI (US); Paul J. Soltys, Lake Zurich, IL (US); Rahul Tandon, Waukegan, IL (US)

(73) Assignee: Baxter International Inc., Deerfield, IL (US)

( * ) Notice: Subject to any disclaimer, the term of this patent is extended or adjusted under 35 U.S.C. 154(b) by 108 days.

(21) Appl. No.: 12/465,214

(22) Filed: May 13, 2009

(65) Prior Publication Data
US 2009/0218288 A1    Sep. 3, 2009

Related U.S. Application Data

(60) Continuation of application No. 11/774,359, filed on Jul. 6, 2007, now Pat. No. 7,955,290, which is a division of application No. 09/990,673, filed on Nov. 13, 2001, now Pat. No. 7,241,272.

(51) Int. Cl.
*A61M 37/00*    (2006.01)

(52) U.S. Cl. .............................. 604/5.01; 604/28; 604/29

(58) Field of Classification Search .................... 604/29, 604/5.01, 5.04, 43
See application file for complete search history.

(56) References Cited

U.S. PATENT DOCUMENTS

| | | | |
|---|---|---|---|
| 3,669,878 A | 6/1972 | Marantz et al. | |
| 3,669,880 A | 6/1972 | Marantz et al. | |
| 3,707,967 A | 1/1973 | Kitrilakis et al. | |
| 3,884,808 A | 5/1975 | Scott | |
| 4,303,521 A | 12/1981 | Lehmann | |
| 4,313,831 A | 2/1982 | Lehmann et al. | |
| 4,364,747 A | 12/1982 | Blackshear et al. | |
| 4,386,611 A | 6/1983 | Kantorski et al. | |
| 4,460,555 A | 7/1984 | Thompson | |
| 4,542,015 A | 9/1985 | Smakman et al. | |
| 4,610,791 A * | 9/1986 | Henne et al. | 210/490 |
| 4,650,587 A | 3/1987 | Polak et al. | |
| 4,659,744 A | 4/1987 | Matsui et al. | |
| 4,661,246 A | 4/1987 | Ash | |
| 4,721,652 A | 1/1988 | Takai et al. | |
| 4,765,907 A | 8/1988 | Scott | |
| 4,806,244 A | 2/1989 | Guilhem | |
| 4,988,569 A | 1/1991 | Okazaki et al. | |
| 5,277,820 A | 1/1994 | Ash | |
| 5,514,281 A | 5/1996 | Boos et al. | |
| 5,536,412 A | 7/1996 | Ash | |
| 5,618,441 A | 4/1997 | Rosa et al. | |

(Continued)

FOREIGN PATENT DOCUMENTS

DE    31 10 128    9/1982

(Continued)

*Primary Examiner* — Laura Bouchelle
(74) *Attorney, Agent, or Firm* — K&L Gates LLP

(57) ABSTRACT

Methods and devices for providing dialysis treatment are provided. The device includes a resin bed including zirconium phosphate, zirconium oxide, and urease.

22 Claims, 21 Drawing Sheets

U.S. PATENT DOCUMENTS

| | | | |
|---|---|---|---|
| 5,618,710 A | 4/1997 | Navia et al. | |
| 5,744,042 A | 4/1998 | Stange et al. | |
| 5,919,369 A | 7/1999 | Ash | |
| 5,944,684 A * | 8/1999 | Roberts et al. | 604/5.04 |
| 6,627,164 B1 | 9/2003 | Wong | |

FOREIGN PATENT DOCUMENTS

| | | |
|---|---|---|
| EP | 0 064 393 | 11/1982 |
| EP | 0 003 914 | 5/1984 |
| FR | 2 585 251 | 1/1987 |
| GB | 2 122 509 | 1/1984 |
| GB | 2 124 511 | 2/1984 |
| JP | 55-32384 | 7/1980 |
| JP | 4-348757 | 3/1992 |
| SU | 1102918 | 1/1983 |
| WO | WO 95/02559 | 1/1995 |

* cited by examiner

METHOD AND COMPOSITION FOR REMOVING UREMIC TOXINS IN DIALYSIS PROCESSES

CROSS-REFERENCE TO RELATED APPLICATIONS

This application is a continuation of U.S. patent application Ser. No. 11/774,359, filed on Jul. 6, 2007, which is a divisional of U.S. patent application Ser. No. 09/990,673, filed Nov. 13, 2001, now U.S. Pat. No. 7,241,272 the entire content of which is expressly incorporated herein by reference.

BACKGROUND

The present invention relates generally to methods of treatment. More specifically, the present invention relates to dialysis processes.

Due to disease or insult or other causes, the renal system can fail. In renal failure of any cause, there are several physiological derangements. The balance of water, minerals (Na, K, Cl, Ca, P, Mg, $SO_4$) and the excretion of daily metabolic load of fixed hydrogen ions is no longer possible in renal failure. During renal failure, toxic end products of nitrogen metabolism (urea, creatinine, uric acid, and others) can accumulate in blood and tissues.

Dialysis processes have been devised for the separation of elements in a solution by diffusion across a semi-permeable membrane (diffusive solute transport) down a concentration gradient. Principally, dialysis comprises two methods: hemodialysis and peritoneal dialysis.

Hemodialysis treatment utilizes the patient's blood to remove waste, toxins, and excess water from the patient. The patient is connected to a hemodialysis machine and the patient's blood is pumped through the machine. Catheters are inserted into the patient's veins and arteries to connect the blood flow to and from the hemodialysis machine. Waste, toxins, and excess water are removed from the patient's blood and the blood is infused back into the patient. Hemodialysis treatments last several hours and are generally performed in a treatment center about three or four times per week.

Peritoneal dialysis utilizes a dialysis solution and dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs due to diffusion and osmosis. The spent dialysate is drained from the patient's peritoneal cavity to remove the waste, toxins, and water from the patient.

There are various types of peritoneal dialysis, including continuous ambulatory peritoneal dialysis (CAPD) and automated peritoneal dialysis (APD). CAPD is a manual dialysis treatment in which the patient connects an implanted catheter to a drain and allows a spent dialysate fluid to drain from the peritoneal cavity. The patient then connects to a bag of fresh dialysate and manually infuses the fresh dialysate through the catheter and into the patient's peritoneal cavity. The patient disconnects the catheter from the fresh dialysate bag and allows the dialysate to dwell within the cavity to transfer waste, toxins, and excess water from the patient's bloodstream to the dialysate solution. After the dwell period, the patient repeats the manual dialysis procedure.

In CAPD the patient performs several drain, fill, and dwell cycles during the day, for example, about four times per day. Each treatment cycle typically takes about 3-4 hours. Manual peritoneal dialysis performed by the patient requires a great deal of time and effort by the patient. The patient is routinely inconvenienced leaving ample opportunity for therapy enhancements to improve patient quality of life.

Automated peritoneal dialysis is similar to continuous peritoneal dialysis in that the dialysis treatment includes a drain, fill, and dwell cycle. However, a dialysis machine automatically performs 3-4 cycles of peritoneal dialysis treatment, typically overnight while the patient sleeps.

To this end, a dialysis machine is fluidly connected to an implanted catheter. The dialysis machine is also fluidly connected to a source of fresh dialysate, such as a bag of dialysate solution, and to a fluid drain. The dialysis machine pumps spent dialysate from the peritoneal cavity though the catheter to the drain. Then, the dialysis machine pumps fresh dialysate from the dialysate source through the catheter and into the patient's peritoneal cavity. The dialysis machine allows the dialysate to dwell within the cavity to transfer waste, toxins, and excess water from the patient's bloodstream to the dialysate solution. The dialysis machine is computer controlled so that the dialysis treatment occurs automatically when the patient is connected to the dialysis machine, for example, overnight.

Several drain, fill, and dwell cycles will occur during the treatment. Also, a last fill is typically used at the end of the automated dialysis treatment so that the patient can disconnect from the dialysis machine and continue daily functions while dialysate remains in the peritoneal cavity. Automated peritoneal dialysis frees the patient from manually performing the drain, dwell, and fill steps, and can improve the patient's dialysis treatment and quality of life.

In view of recent developments and therapies, the line between traditional peritoneal dialysis and hemodialysis has become blurred. For example, some therapies use components of both therapies.

A recent therapy is regenerative dialysis. In this system a dialysis system is used that includes a cartridge for dialysate regeneration. The cartridge includes a resin bed including zirconium-based resins. An example of a cartridge that is used in such a system is manufactured under the name Redy by Sorb Technology, Oklahoma City, Okla. This system, however, requires the constant attention of medical personnel. Moreover, the dialysate that is regenerated by the cartridge has an undesirable sodium and pH level. In this regard, the dialysis solution does not have a physiologic pH or electrolyte content. This is especially a problem if the dialysis solution is to be reinfused into the peritoneal cavity of a patient.

SUMMARY

The present invention provides improved systems as well as methods for providing dialysis to a patient. More specifically, in an embodiment, the present invention provides systems, cartridges, and methods for regenerative dialysis therapies. However, it should be noted that the cartridge of the present invention can be used in a variety of therapies including hemodialysis and peritoneal dialysis therapies as well as acute dialysis.

To this end, in an embodiment, a device for removing uremic toxins in a dialysis procedure is provided comprising a body having an inlet and an outlet and defining an interior, the interior including a layer comprising urease, a layer comprising zirconium oxide, a layer comprising zirconium phosphate, and a layer comprising carbon, and the device being so constructed and arranged so that a fluid entering the device contacts the zirconium oxide layer upon entering the device before contacting the urease or the zirconium phosphate layer.

In an embodiment, the zirconium oxide is in bicarbonate form.

In an embodiment, the zirconium oxide is in hydroxyl form.

In an embodiment, the carbon layer is located in juxtaposition to the outlet.

In an embodiment, the fluid flows through a layer of zirconium oxide before entering the carbon layer.

In an embodiment, the zirconium phosphate has a pH of approximately 2 to about 8.

In an embodiment, the zirconium oxide has a pH of approximately 6 to about 13.

In an embodiment, two separate layers of zirconium phosphate are provided.

In an embodiment, two separate layers of zirconium oxide are provided.

In an embodiment, open headers at each of the inlet and outlet end of the device are provided.

In an embodiment, an opening for venting a gas to the atmosphere located at the outlet end is provided.

In an embodiment the urease layer is the first layer.

In an embodiment the zirconium phosphate layer is located before the zirconium oxide layer.

In a further embodiment of the present invention, a cartridge for use in a dialysis system for removing toxins is provided comprising a body having an inlet end and an outlet end. The body includes an interior including at least four layers, the layers including a first layer of a resin selected from the group consisting of zirconium phosphate having a pH of approximately 2.5 to about 5 and urease, a second layer of a resin selected from the group consisting of zirconium oxide having a pH of approximately 9 to about 13 and urease, a third layer of zirconium phosphate, and a fourth layer of zirconium oxide having a pH of approximately 6.5 to about 7.5. The interior is so constructed and arranged that a fluid entering the interior from the first inlet end flows through the first layer, then the second layer, then the third layer, and then the fourth layer.

In an embodiment, the first layer comprises approximately 200 to about 800 grams of zirconium phosphate.

In an embodiment, the fourth layer comprises approximately 50 to about 200 grams of carbon.

In an embodiment, the urease is a cross-linked enzyme.

In yet another embodiment, a device for regenerating a dialysis solution is provided. The device includes a body including a resin bed. The resin bed includes at least a layer of urease, zirconium phosphate, zirconium oxide, and carbon and being so constructed and arranged that a dialysis solution having a pH that is either basic or acidic will exit the cartridge after it passes through the resin bed at a pH of approximately 7 to about 7.8.

In an embodiment, the first layer of the resin bed that the solution contacts is selected from the group consisting of zirconium phosphate having a pH of approximately 2.0 to about 5 and urease.

In an embodiment, the second layer that the solution passes through in the resin bed is selected from the group consisting of zirconium oxide having a pH of approximately 9 to about 13 and urease.

In an embodiment, the third layer of the resin bed that the solution passes through is zirconium phosphate.

In an embodiment, the fourth layer of the cartridge that the solution passes through is zirconium oxide having a pH of approximately 6.8 to about 7.5.

In an embodiment, the pH of the solution exiting the cartridge is approximately 7.4.

In a further embodiment, a device for use in a system for treating a patient with a dialysis solution is provided. The device including an inlet in fluid communication with a source of dialysis solution, a body including the inlet and defining an interior and having an outlet, and the body including a resin bed including a layer of urease, a layer of zirconium oxide, and a layer of zirconium phosphate that define a three layer structure. The resin bed is oriented so that the first layer that the dialysis solution contacts of the three layer structure is either the urease or the zirconium phosphate layer and the zirconium oxide layer is so constructed and arranged that a basic or an acidic dialysis solution entering the inlet will exit the outlet with a physiologically acceptable pH.

In an embodiment, the device is used in a regenerative dialysis system.

Still further, in an embodiment, a method for constructing a cartridge for use in a system for providing dialysis is provided. The method comprising the steps of providing a resin bed including zirconium oxide and zirconium phosphate and selecting and orienting the zirconium oxide and zirconium phosphate to allow the cartridge to remove uremic toxins present in a dialysis solution entering the resin bed and causing the dialysis solution exiting the cartridge to be at a physiological pH and include a physiological electrolyte balance.

In an embodiment, the method includes the steps of providing a body having an inlet and an outlet and defining an interior, the interior including a layer comprising urease, a layer comprising zirconium oxide, a layer comprising zirconium phosphate, and a layer comprising carbon; and the device being so constructed and arranged so that a fluid entering the device contacts the zirconium phosphate layer upon entering the device before contacting the urease on the zirconium oxide layer.

In a yet further embodiment, a method for providing dialysis is provided comprising the steps of removing uremic toxins by passing a dialysis fluid through a body having an inlet and an outlet and defining an interior, the interior including at least four layers, a first layer comprising either zirconium phosphate having a pH of approximately 2.5 to about 5 or urease, a second layer comprising either zirconium oxide having a pH of approximately 9 to about 13 or urease, a third layer comprising zirconium phosphate and a fourth layer comprising zirconium oxide having a pH of approximately 6.8 to about 7.5.

Additionally, in an embodiment, a method of providing regenerative dialysis is provided comprising the step of removing uremic toxins by passing a dialysis fluid through a body having an inlet and an outlet and defining an interior, the interior including at least four layers, a first layer comprising either zirconium phosphate having a pH of approximately 2.5 to about 5 or urease, a second layer comprising either zirconium oxide having a pH of approximately 9 to about 13 or urease, a third layer comprising zirconium phosphate and a fourth layer comprising zirconium oxide having a pH of approximately 6.8 to about 7.5.

An advantage of the present invention is to provide an improved dialysis procedure.

Moreover, an advantage of the present invention is to provide an improved cartridge for removing impurities from a dialysis fluid.

Still, an advantage of the present invention is to provide an improved system for providing dialysis.

Further, an advantage of the present invention is to provide an improved cartridge that can be used in a single loop or multiple loop system.

Additionally, an advantage of the present invention is to provide an improved resin bed for a cartridge for a dialysis system.

Additionally, an advantage of the present invention is to provide an improved cartridge that is constructed and arranged so that dialysis solution that exits the cartridge has a physiological pH and electrolyte content.

Additional features and advantages are described herein, and will be apparent from, the following Detailed Description and the figures.

DETAILED DESCRIPTION

The present invention relates to methods of providing dialysis treatment. Additionally, the present invention relates to systems for providing dialysis. More specifically, in an embodiment, the present invention provides improved cartridges that are used to remove uremic toxins.

In a preferred embodiment, the present invention relates to systems and components for use in continuous flow peritoneal dialysis procedure. However, it should be noted that the present invention can be used in a variety of methods for providing dialysis including hemodialysis and peritoneal dialysis Continuous flow peritoneal dialysis is achieved by continuously infusing into and draining from the peritoneum a solution. For example, a closed loop or recirculating dialysis can be used where the solution is continuously recirculated to the patient. This can have the advantage of substantially reducing the amount of solution needed for a treatment. However, it is necessary to regenerate the solution with the exact glucose and electrolyte requirements required by the patient. This therapy is designed to be performed primarily at night.

Figure 1:
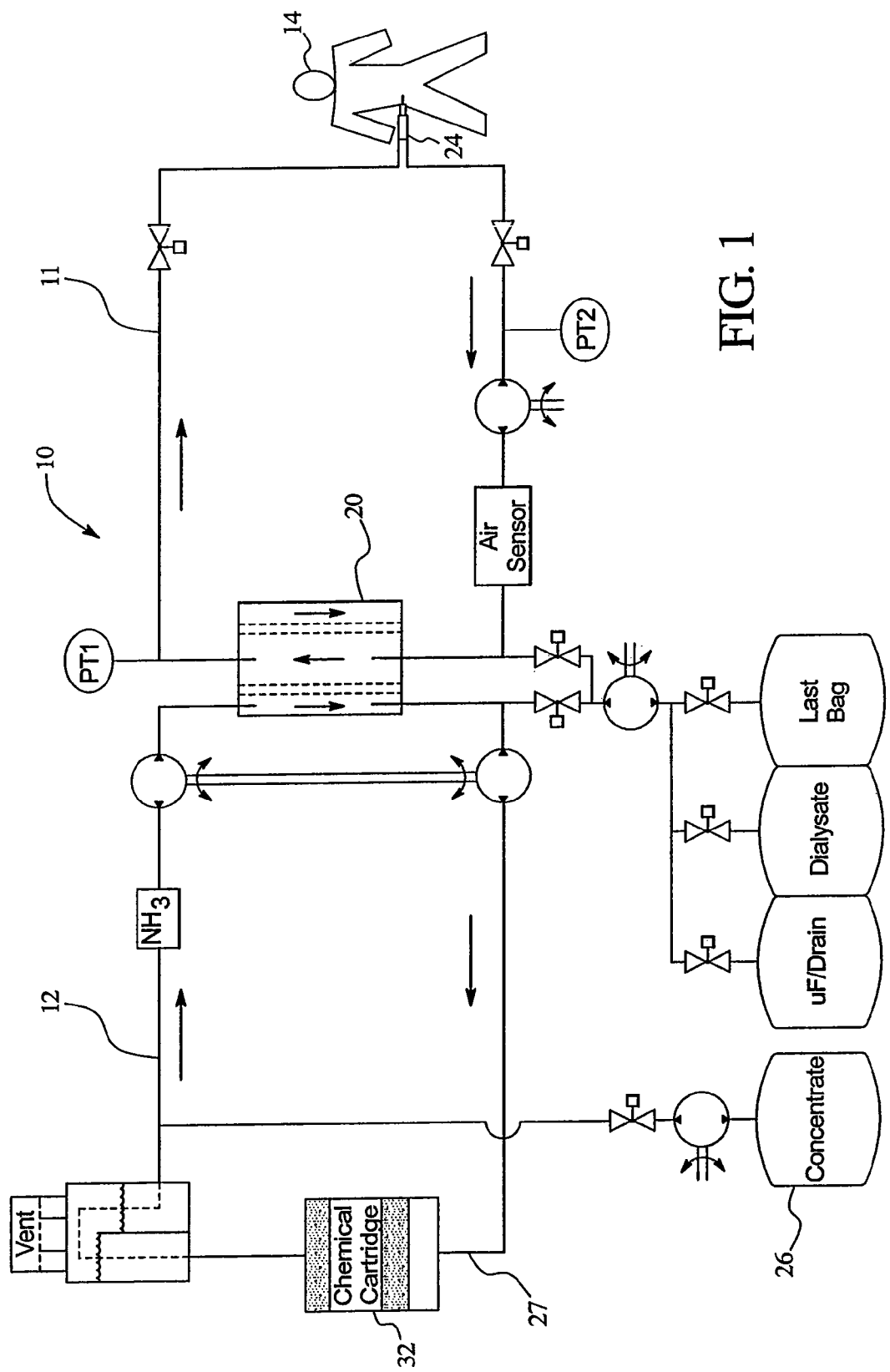
FIG. 1 illustrates schematically a system for performing dialysis pursuant to the present invention.

Generally, the system comprises a disposable set including a pump cassette, cartridge, dialyzer, and solution concentrate. FIG. 1 illustrates generally a schematic of the system 10 for providing dialysis treatment pursuant to the present invention.

As illustrated in FIG. 1, two loops are provided: a patient loop 11; and a regeneration loop 12. However, it should be noted that the present invention can be used in a system including only one loop or more than two loops. The patient loop 11 is used to dialyze the patient 14 with dialysate. The regeneration loop 12 is used to regenerate the dialysate. As illustrated generally, the dialysate is pumped from a bag 16 in the patient loop 11 into the patient 14 through a catheter 24. Spent fluid is then fed from the patient 14 back into the dialyzer 20.

A variety of components can be used in the patient loop. In a preferred embodiment a dual lumen catheter 24 is used. The dual lumen catheter provides for continuous, flow in to and out of the peritoneal cavity of the patient. To this end, the dual lumen catheter is implanted in the patient. An example of a catheter for use in the system 10 of the present invention is disclosed in U.S. patent application Ser. No. 09/689,508, filed on Oct. 12, 2000, and entitled "Peritoneal Dialysis Catheter," the disclosure of which is incorporated herein by reference. However, it should be noted that two single lumen catheters can be used as well as a single lumen catheter.

To regenerate the dialysate, the regeneration loop 12 is provided. In the embodiment illustrated, the regeneration loop 12 preferably includes concentrate in a container 26, a cartridge 32, an ultrafiltrate (UF) pump, and a UF collection means that communicates with the patient loop 11 via the dialyzer 20. A concentrate pump is provided to pump the concentrate 26 from the container through fluid path 27. The fluid in the regeneration loop is pumped through the dialyzer 20 in a counter current fashion to the fluid in the patient loop 11.

The dialyzer 20 is provided to remove water and small solutes such as urea, and creatinine from spent dialysate in the patient loop 11. The dialyzer 20 provides a sterile independent barrier between the patient loop 11 and the regeneration loop 12. Any dialyzer 20 can be used that provides a high clearance of small molecules across the dialyzer. Uric acid will diffuse across the dialyzer, ultrafiltrate is also removed.

It should be noted that although the cartridge 32 of the present invention is illustrated as being used in a two loop system, it can be used in other systems. For example, it is envisioned that the cartridge can be used in a one loop system.

Figure 2:
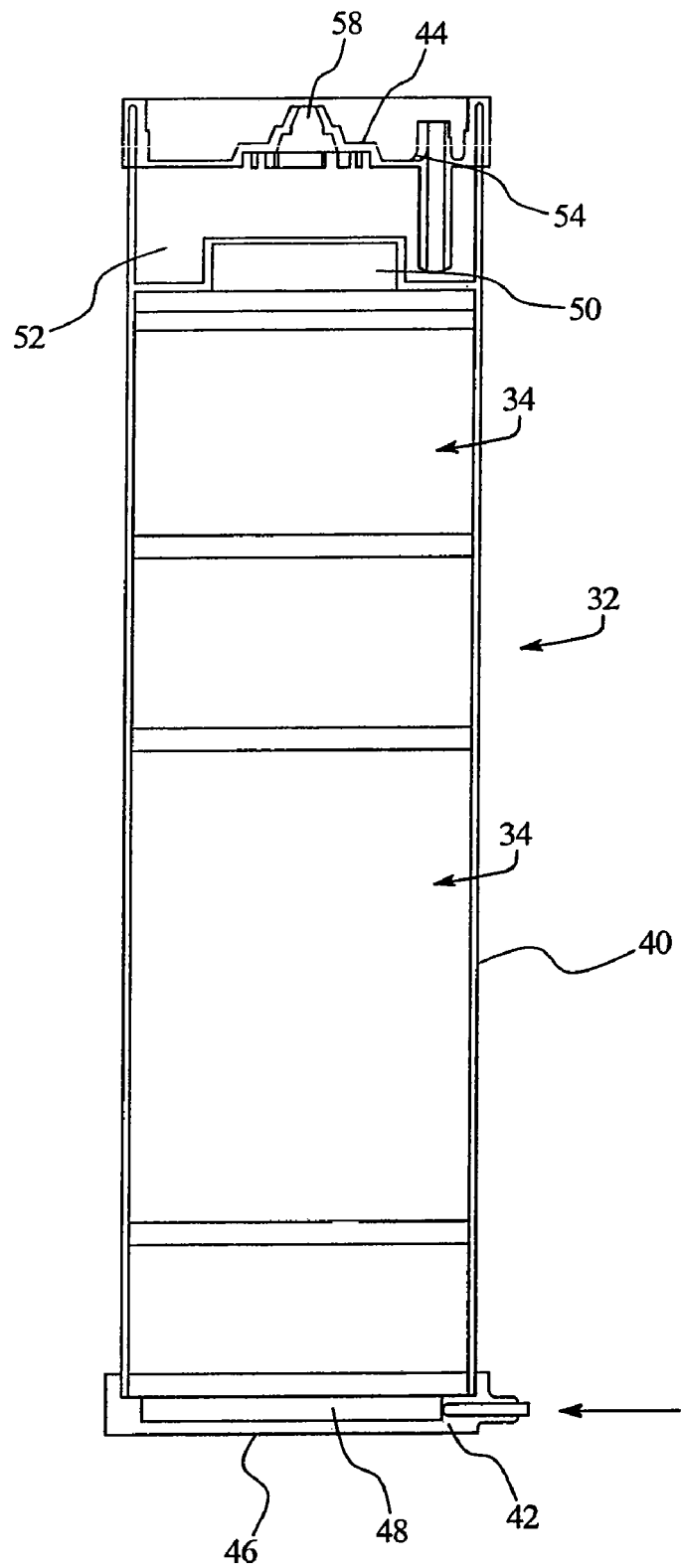
FIG. 2 illustrates a cross-sectional view of an embodiment of the cartridge of the present invention.

Referring now to FIG. 2, a cross-sectional view of an embodiment of the cartridge 32 of the present invention is illustrated. The cartridge 32 includes a resin bed 34 that is designed to modify the chemistry of the recirculating dialysate and remove uremic toxins. At the same time, pursuant to the present invention, the cartridge 32 maintains electrolyte concentrations and the solution pH of the dialysate at physiologic levels.

The cartridge 32 generally comprises: a main body 40, an inlet cap 42, the resin bed 34, and an outlet cap 44. In the embodiment illustrated, fluid is routed into the cartridge 32 through the inlet cap 42 that is located at a bottom 46 of the cartridge 32. In the embodiment illustrated, a small open header chamber 48 prior to the resin bed 34 is used to distribute the flow of fluid evenly across the cross-section of the cartridge 32 and thereby the resin bed 34. The fluid preferably flows upwardly through the resin bed 34.

In the embodiment illustrated, downstream of the final section of the resin bed 34 there is located another open header chamber 50. The second open header chamber 50 is located before a gas separation chamber 52. The second header chamber 50 is used to maintain an even fluid velocity distribution throughout the resin bed 34.

The liquid level in the gas separation chamber 52 is maintained within a specified range to provide an air space above the liquid in the cartridge 32. Gases that are produced during therapy, e.g., carbon dioxide, are vented from the cartridge 32 to the environment through a passage 54 on the outlet cap 44. If desired, this passage 54 may include a filter member. A submerged, or partially submerged, barrier in the gas separation chamber 52 produces a flow pattern that restricts gases from being drawn to the liquid outlet.

At the outlet cap 44 of the cartridge 32 the liquid outlet port 58 is located. The liquid outlet 58 port removes liquid from the chamber of the cartridge 32 through the outlet cap 44 using a siphon action. If desired, an additional port may be used to add a chemical concentrate to the volume of liquid in the gas separation chamber to reconstitute the chemical composition of the fluid outflow.

In an embodiment, the interior of the cartridge 32 has a rough surface. The rough surface is designed so that it prevents fluid from flowing along the sides of the exterior by passing the resin bed 34.

The resin bed 34, in part, functions to remove waste. In this regard, generally waste is removed using a two-step process. The steps consist of an enzymatic conversion of urea using urease followed by subsequent removal of the conversion byproducts. In the enzymatic reaction, one mole of urea is decomposed into two moles of ammonia and one mole of carbon dioxide. Ammonia ($NH_3$) is primarily (>95%) present as ammonium ion ($NH_4^+$), since its pH of 9.3 is substantially greater than the solution pH. The carbon dioxide that is formed can either be present as dissolved carbon dioxide or as bicarbonate ion, depending on the solution pH. Since the pH for this equilibrium is 6.1, both species may be present in substantial quantities under conditions of use. In addition, if the solution is in communication with a gas phase, the dissolved carbon dioxide is in equilibrium with the carbon dioxide present in the gas phase.

The resin bed includes at least four layers, although more layers can be used. Generally, the layers of the resin bed comprise at least: a urease layer; a layer of zirconium phosphate; a layer of zirconium oxide; and a layer of carbon.

The purpose of the urease layer is to enzymatically convert urea that is present in the solution that is flowing through the resin bed 34 to ammonia and carbon dioxide. In solution, ammonia acts as a base since the formation of ammonium results from the donation of $H^+$. Similarly carbon dioxide ($CO_2$) acts as an acid, since the formation of bicarbonate ($HCO_3$) donates H+ to solution. The net result of the urease reaction is to increase the pH.

In an embodiment, 25 to 250 mg of urease are used, although any amount of urease can be used that is sufficient to convert the urea present in the solution to ammonia and carbon dioxide. Preferably, urease comprises the first or second layer of the resin bed.

A variety of urease materials can be used. For example, crosslinked enzyme crystals of urease (Urease-CLEC) can be used. This material is ultra pure and has high specific activity. Therefore, a very small quantity of this urease is sufficient to provide the desired urea-conversions.

By way of example, the amount of urease-CLEC required was optimized for two different internal diameters of the cartridge, 3¼" and 1¼" respectively. Next, in order to determine the optimal contact time between urease-CLEC and the substrate stream, the enzyme was blended with powdered Zirconium Oxide (ZO). Table 1 shows the optimized amount of urease-CLEC and ZO required to obtain a urea conversion >90%. The quantity of enzyme used was stable to sterilization with 40 kGy γ-radiation. The flow rate used in all above experiments was 100 ml/min.

TABLE 1

Summary of urease-CLEC required for urea conversion

| Column Diameter (inch) | Amount of urease-CLEC required (mg) | Amount of ZO required (gm) | γ-sterilization dose (kGy) | % Urea Conversion |
|---|---|---|---|---|
| 1.25 | 50 | 25 | >40 | 90 |
| 3.25 | 150 | 150 | >40 | 97 |

For this particular approach of using urease-CLEC, the primary challenge is in the development of procedures for blending very small quantities of urease-CLEC with large quantities of ZO. Where as, the small quantity is advantageous for easy containment within the polymer matrix of an ultrafiltration membrane. The use of these urease-impregnated ultrafiltration membranes provide several benefits over the currently available methods:
1) Better urease containment.
2) Reduced cartridge size resulting in enhanced ease of use by patient.
3) Ease of use during cartridge manufacture
4) Increased safety over the existing system (due to better containment of urease in the cartridge)

Table 2 shows the urea conversion observed at various flow rates using a urease-CLEC impregnated membrane. The membrane tested had a diameter of 1 inch, thus, the flow rates used were 1.3, 2.7 and 5.3 ml/min, which correspond to a flux of 50, 100 and 200 ml/min through a 3.25 inch membrane.

TABLE 2

Sample results obtained from a γ-sterilized urease-CLEC-impregnated membrane

| Amount of Urease-CLEC (mg) | Membrane diameter (inch) | Flow rate (ml/min) | γ-sterilization dose (kGy) | % Urea Conversion |
|---|---|---|---|---|
| 15.85 | 1 | 1.3 | 40 | 87.3 |
| 15.85 | 1 | 2.7 | 40 | 79.2 |
| 15.85 | 1 | 5.3 | 40 | 66.9 |

Although, the urea conversions observed are lower than required, better conversions can be expected from membranes prepared with larger quantities of urease-CLEC. Additionally by employing two membranes in each cartridge a higher overall urea conversion can be obtained.

By way of further example, alumina-stabilized urease can also be used. Upon wetting, the urease dissolves but, it is immediately absorbed by the alumina particles that are located in close proximity. The end result is urease that is physically absorbed by the alumina in close proximity. This urease exposed to γ-irradiation at a dose of 15 kGy in the presence of γ-irradiation retained 75% of its initial activity.

Referring now to the zirconium phosphate layer, zirconium phosphate can absorb, under certain conditions, ammonium ion, calcium, magnesium, and sodium. Ammonium ion is removed from solution via an ion exchange process using zirconium phosphate. Zirconium phosphate contains two counter-ions—hydrogen ($H^+$) and sodium ($Na^+$). Release of the counter-ions is determined by the solution pH and the current loading state of the resin. In addition to its role as an ion exchange resin, zirconium phosphate also has a considerable buffering capacity.

If the loading state pH of the resin is 6.2 then when in contact with an (acidic) solution having a pH of less than 6.2, the resin will release $Na^+$ in exchange for $H^+$, even in the absence of any other ions. In contact with a (basic) solution having a pH of greater than 6.2, the resin will release $H^+$ in exchange for $Na^+$, even in the presence of other cations. In contact with a solution having a pH of 6.2 and containing ammonium, the resin will exchange a mixture of $Na^+$ and $H^+$ ions for $NH_4^+$ such that its equilibrated pH remains unchanged. The zirconium phosphate resin possesses excellent capacity for ammonium, and this capacity is unaffected by changes in equilibrated pH within a given range (pH 6.0-7.2).

The desired pH of the zirconium phosphate will depend, in part, on its location in the resin bed, e.g., the component it is designed to remove. To this end, the zirconium phosphate layer can have a pH of between approximately 2 to about 8. Preferably, zirconium phosphate is present in a range of approximately 200 to about 800 grams. The amount of zirconium phosphate necessary is at a minimum that amount that is sufficient to remove the ammonium that is generated. The level of ammonium generated is determined by the urea that is to be removed by the cartridge. Thus, the amount of zirconium phosphate equals the ammonium to be removed divided by the capacity of the zirconium phosphate, to remove ammonium, which can be determined experimentally.

Figure 3:
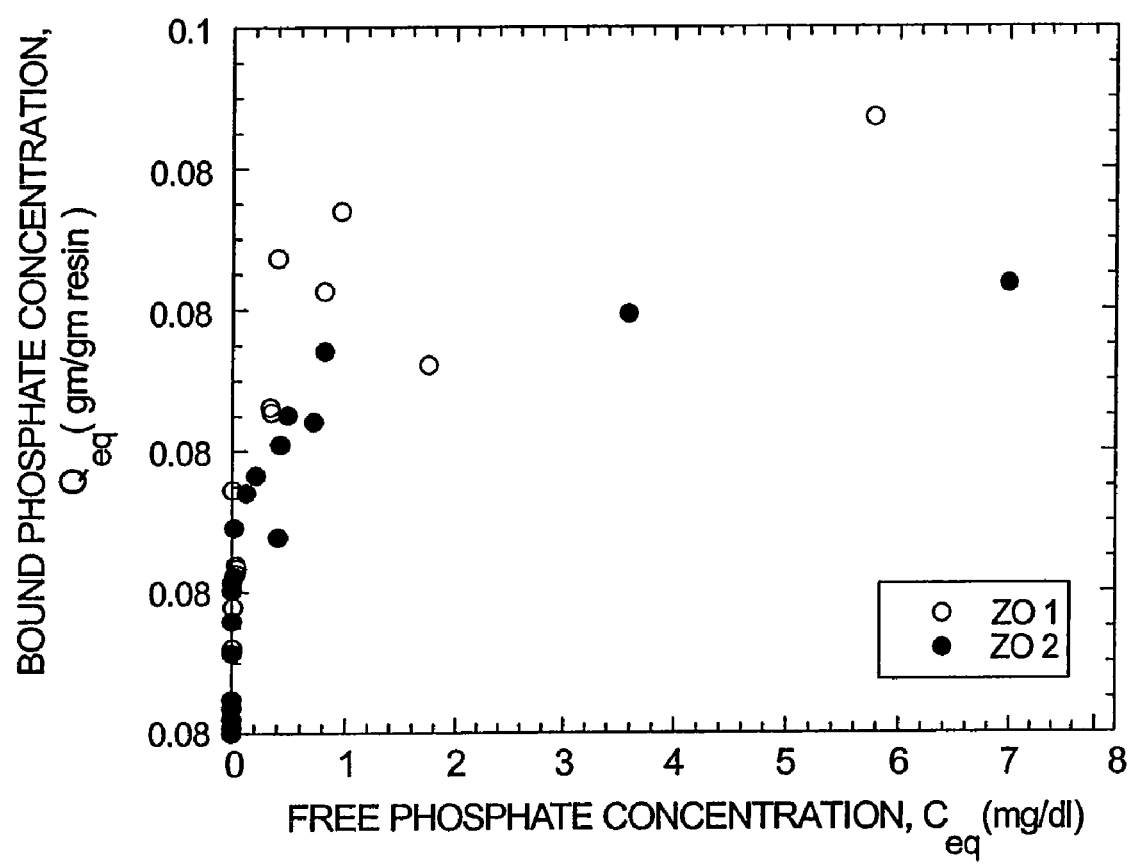
FIG. 3 illustrates graphically ammonium effluent concentration (ppm) versus mass ammonium delivered (mEq) for zirconium phosphate available from two suppliers (Sorb technologies and magnesium elektron).

For example, a process for determining the quantity of zirconium phosphate required in the device can be determined as follows. Equilibrium data is employed to make a first pass guess at the amount of zirconium phosphate required. For a given cartridge containing a particular amount of zirconium phosphate, the effluent ammonium concentration profile is obtained. The capacity of a given cartridge is defined as the mass of ammonium delivered at the time that the effluent concentration exceeds a prescribed level. In an embodiment, this effluent cutoff level is set at 20 ppm. For example, in the data from FIG. 3, for a small prototype device, the ammonium capacity is approximately 4.2 mEq for 10.5 g zirconium phosphate, an input concentration of 3.9 mEq/L ammonium, and a bulk flow rate of 8.3 mL/min (breakthrough at the 20 ppm level occurs after absorption of 4.2 mEq ammonium).

In an embodiment, it is believed that the quantity of zirconium phosphate required is on the order of approximately 600 to about 800 g. In an embodiment, zirconium phosphate will comprise more than half of the cartridge by weight. As to its location in the resin bed, preferably zirconium phosphate can comprise the first layer through all but the last layer of the resin bed (not including the carbon layer). Moreover, multiple zirconium phosphate layers can be used.

Referring now to the zirconium oxide layer, zirconium oxide resin is an amphoteric resin. This means that the resin's ion exchange properties are dependent on the solution pH. If the solution pH is much lower than the pH of the resin, the resin acts as an anion exchange resin. If the solution pH is much greater than the pH of the resin, the resin acts as a cation exchange resin. If the solution pH is near its pH, the resin demonstrates properties of a mixed bed, exchanging both cations and anions. This latter behavior of a mixed bed occurs throughout the physiologic pH range.

The zirconium oxide layer removes phosphates. The zirconium oxide layer, depending on the pH, can also function to remove sodium. Preferably the zirconium oxide layer has a pH of approximately 6 to about 13.

Figure 4:
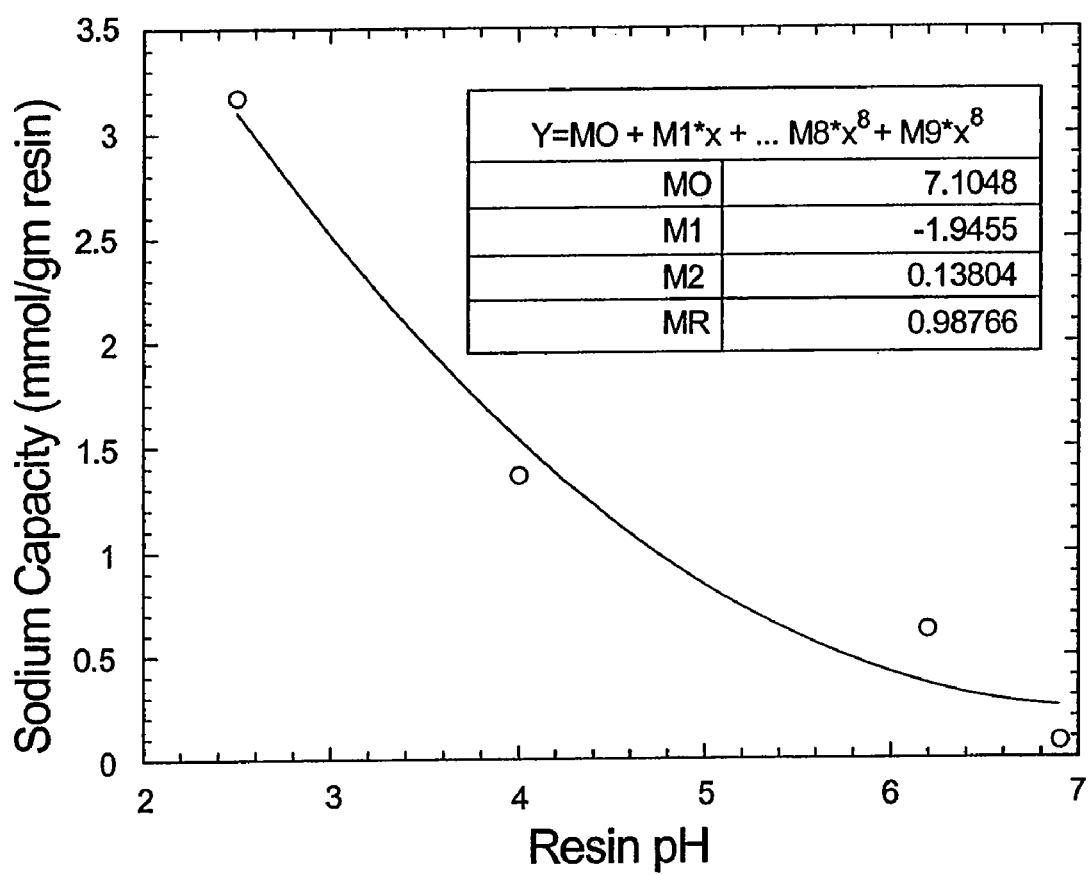
FIG. 4 illustrates graphically sodium capacity as a function of zirconium oxide pH.

The phosphate capacity of the resin is very high, thus, the size of the layer is governed by how much sodium needs to be removed. In like fashion, the amount of zirconium oxide is thereby determined by the capacity of the zirconium oxide that is used to remove sodium. FIG. 4 illustrates graphically the sodium capacity of zirconium oxide as a function of its pH.

The zirconium oxide layer functions to remove any phosphate that may not have been absorbed by the other components of the resin bed. Further, the zirconium oxide layer controls the pH of the solution leaving the cartridge. Accordingly, preferably the zirconium oxide layer, if it is the last layer (not including the carbon layer) of the cartridge 32, has a pH of approximately 7 to about 9 and in a preferred embodiment, approximately 7.4. Although preferably the zirconium oxide layer is the last layer (not including the carbon layer), multiple zirconium oxide layers can be used.

In an embodiment, zirconium oxide is utilized that has been modified by removing the nitrate ion as the counter ion. In this regard, the nitrate ion was exchanged with bicarbonate ion by treating the zirconium oxide with 15% sodium carbonate solution to a pH of approximately 11.3. The mixture was then washed extensively with water to remove residue sodium nitrate and sodium carbonate. The resin was then dried under high vacuum at an RT of approximately 24 hours. The resulting resin (0.5 g/mL in water) at a pH of approximately 8.5, and a conductivity of 155.1 us/cm. The dried resin was further modified by suspending the resin in water and adding hydrochloric acid until a pH of 7 was achieved. Following the pH adjustment, the resin was washed to remove residual chloride and sodium ions. After each of the washing steps the resin filtrate pH and conductivity was measured. After wash 1, the paper pH was 6.5 to 7 and conductivity 464 us/cm; after wash 2, paper pH 6.5 to 7 and conductivity 186.5 us/cm; and wash 3 pH (paper) 6.5 to 7, conductivity 38.2 us/cm. It should be noted that washes 1 and 2 were performed by letting the mixture settle and then decanting the supernatant to waste. After wash 3, the solid was collected via vacuum filtration through a 0.2 micron pore size nylon filter. The solid was dried via vacuum on the filter apparatus between 6 to 12 hours to yield the final product.

Referring now to the carbon layer, carbon removes creatinine, uric acid or other organic molecules that still may be present in the solution. For example, the carbon layer removes creatinine. The amount of creatinine that needs to be removed by this cartridge is approximately 0.5 g to about 3.0 g. Although the volume of carbon can comprise a wide range, preferably approximately 50 to about 200 grams of carbon is used. Preferably, the carbon will be of the type that has the ability to remove less than 30 grams of glucose from the peritoneal dialysis solution. Thus, such a carbon layer will not remove an excess amount of glucose from the dialysis solution. Activated carbon sold under the designation LP-50 by Carbochem, Ardmore, Pa., has been found to function satisfactorily in this regard. Other carbons can be used. It is believed that carbons that are coconut shell based having a particle size of 20×50 will also work. It should be noted that the carbon layer can be located as any of the layers in the resin bed, although in a preferred embodiment it is the last layer.

Figure 5:
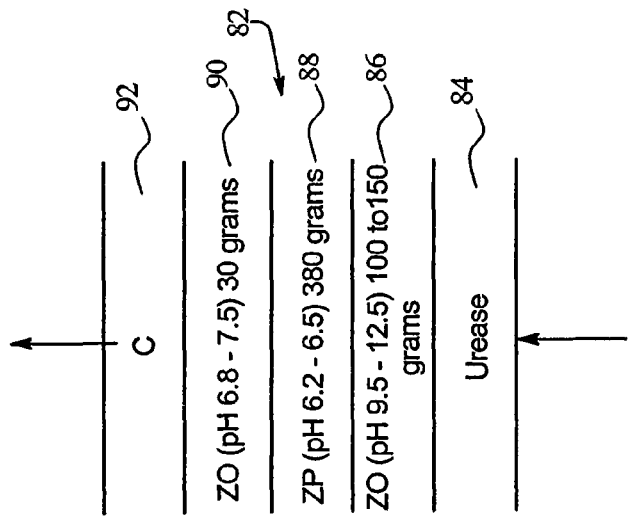
FIG. 5 illustrates an embodiment of a cross-sectional view of a resin bed of a cartridge of the present invention.

FIG. 5 illustrates an embodiment of the resin bed 34 of the present invention. The resin bed 34, in the illustrated embodiment includes five layers 60, 62, 63, 64, and 66. The first layer 60 is a zirconium phosphate layer having a pH of approximately 2.5 to about 5 and comprising approximately 160 grams. The second layer 62 is a layer of urease comprising approximately 25-250 mg of urease-CLEC in 25 gm zirconium phosphate/zirconium oxide or 50-100 gm of urease which is not crosslinked from other sources. The third layer 63 comprises zirconium phosphate having a pH of approximately 7 to about 7.5; preferably there are approximately 380 grams of zirconium phosphate. The fourth layer 64 is approximately 50 to about 75 grams of zirconium oxide at a pH of approximately 5 to about 7.5. The last layer 66 comprises approximately 50 to about 200 grams of carbon and in an embodiment, 130 grams.

In the resin bed 34 the first layer 60 is used to remove sodium, Ca, and Mg. Also this layer 60 will adjust the pH of the solution facilitating the conversion of urea to ammonium by the urease, second layer 62. The third layer 63 removes the ammonium generated by the urease layer 62. To this end, the zirconium phosphate needs to have a pH of greater than or equal to 5; in the illustrated embodiment the pH is 7 to 7.5. The fourth layer 64 of zirconium oxide removes the phosphate and adjusts the pH to approximately 7.4. The size of the fourth layer 64 needs to be such so as to allow the pH of the solution that exists the resin bed 34 to be adjusted to the desired pH. The last layer 66 is the carbon layer that removes any remaining impurities including creatinine.

In CFPD it is required to remove anywhere from approximately 5 to about 20 gm urea/day. Table 1 below provides the amount of resin required for the various layers in order to remove 5, 10, and 20 gm of urea.

For example, removal of 10 gm of urea generates 342 mmol of ammonia and 171 mmol of bicarbonate. Using the resin bed of FIG. 4 to remove 342 mmol of ammonia, a 380 gm layer of zirconium phosphate (resin pH=6.2, ammonia capacity=0.9 mmol/gm resin) was found to be necessary. In the process of removing the 342 mmol of ammonia the resin will release 342 mmol of sodium into the solution. Zirconium phosphate at pH of 6.2 has a capacity of 0.63 mmol/gm resin for sodium and hence will re-adsorb 342-127 mmol of sodium. As a result, an additional 127 mmol of sodium needs to be removed from the solution after passing through layer 63. Layer 60, which is also made up of zirconium phosphate removes this amount of sodium. The amount of zirconium phosphate required to remove this amount of sodium varies as a function of pH of the resin. Table 3 shows the amount of zirconium phosphate at various pHs required to remove 127 mmol of sodium. The amount of zirconium phosphate at various pHs required to remove sodium is equal to:

sodium capacity (mmol/gm resin)=7.1-1.945 (pH of ZP) and 0.138 (pH of Zp)$^2$.

Accordingly, at a pH of 2.5, the sodium capacity is 3.1 mmol/gm ZP. From Table 3, at a pH of 7.2, to remove 171 mmol of sodium we need 53.4 gm of zirconium phosphate.

The size of the zirconium oxide layer is controlled by the amount required to raise the pH from 6.2 to neutral during the entire therapy time. This amount is easily obtained from the pH profile curve. A gram of zirconium oxide resin has the capacity to raise the pH of approximately 0.45 L of solution from 6.2 to neutral. In an embodiment of a dialysis method it is necessary to process 48 L of the solution in 8 hr, resulting in a requirement of 106 gm of resin. The amount of zirconium oxide resin required to remove all of the phosphate in the solution was found to be in the range of 60-80 gm. Thus the 106 gm of zirconium oxide required to adjust the pH will also meet the requirement for the removal of phosphate.

TABLE 3

Amount of Resin for 5, 10, 20 gm Urea Removed

| ZP Layer 3 PH | Ammonia to be removed mmol | ZP Layer 3 size (gm) | Sodium to be removed (mmol) | ZP layer size at various pHs (gm) | | | ZO Layer 4 size(gm) |
|---|---|---|---|---|---|---|---|
| | | | | 2.5 | 4.0 | 5.0 | |
| 7.2 | 171 | 285 | 171 | 53.4 | 114 | 190 | 60-80 |
| 6.2 | 171 | 285 | — | — | — | — | 80-100 |
| 7.2 | 342 | 380 | 342 | 107 | 228 | 380 | 60-80 |
| 6.2 | 342 | 380 | 127 | 40 | 85 | 141 | 106 |
| 7.2 | 684 | 456 | 684 | 213 | 456 | 760 | 80-100 |
| 6.2 | 684 | 456 | 396.7 | 124 | 264 | 441 | 130 |

Figure 6:
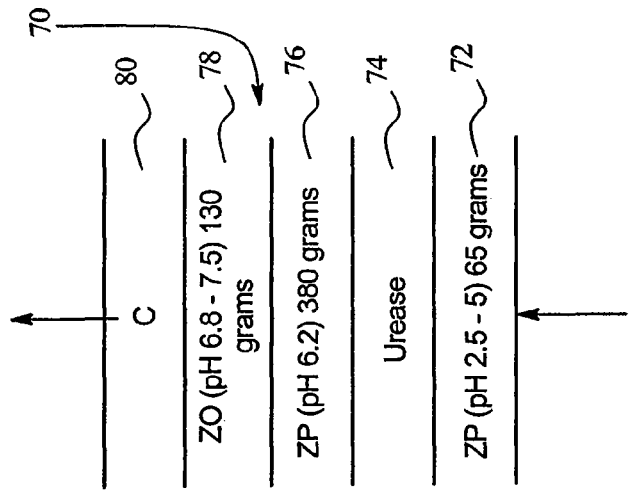
FIG. 6 illustrates a further embodiment of a resin bed of a cartridge of the present invention.

Referring now to FIG. 6 another embodiment of the resin bed of the present invention is illustrated. The resin bed 70 includes a five layer structure. The layers are similar to the resin bed 34 of FIG. 4. In this regard, the first layer 72 is zirconium phosphate, the second layer 74 is urease, the third layer 76 is zirconium phosphate, the fourth layer 78 is zirconium oxide, and the fifth layer 80 is carbon.

However, the first 72, third 76, and fourth 78 layers are slightly different than their counterparts in FIG. 4. In this regard, the first layer 72 of zirconium phosphate preferably comprises 65 grams having a pH of approximately 2.5 to about 5. The third layer of zirconium phosphate has a pH of greater than 5 and in a preferred embodiment 6.2. This layer also comprises, as in the embodiment of FIG. 4, 380 grams. The fourth layer of zirconium oxide comprises approximately 130 grams and has a pH of approximately 6.8 to about 7.5.

In the resin bed 70, once again, the first layer 72 removes the sodium but does not remove the ammonium. The first layer 72 will also adjust the pH of the solution for converting urea to ammonium by the urease layer. The pH of the solution coming out of the first layer 72 will be approximately the pH of the resin. The lower the pH of the resin, the more sodium is removed. As the solution exits the urease layer 74 and enters the third layer 76 of zirconium phosphate, the ammonium is removed. As the pH of the zirconium phosphate is increased, more ammonium is removed. A pH of at least 5 is required in order to remove the ammonium. Once again, the fourth layer 74 of zirconium oxide removes the phosphate and adjusts the pH to 7.4. The last layer 80, the carbon layer, once again removes any remaining impurities.

Figure 7:
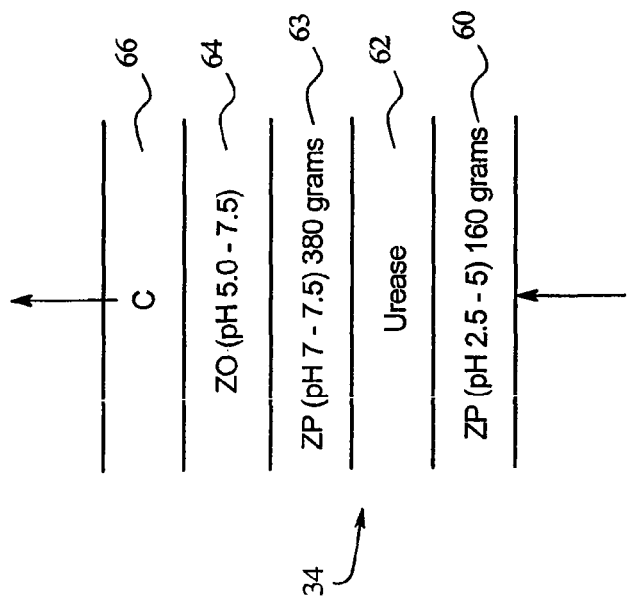
FIG. 7 illustrates a still further embodiment of a resin bed of a cartridge of the present invention.

Referring now to, FIG. 7, a further embodiment of a resin bed 82 is illustrated. In this embodiment, the first layer 84 comprises urease. The second layer 86, in an embodiment, comprises zirconium oxide at a pH of approximately 9.5 to about 12.5. Preferably 100 to 150 grams of zirconium oxide are present. The third layer 88 comprises zirconium phosphate at a pH of approximately 6.2 to about 6.5. Approximately 680 grams are present. The fourth layer 90 comprises zirconium oxide at a pH of approximately 6.8 to about 7.5 with preferably approximately 30 grams being present. The last layer 92 comprises carbon.

In the resin bed 82 the zirconium oxide layer 86 functions in the role of zirconium phosphate in the other resin beds (34 and 70). To this end, it removes the sodium. The amount of sodium removed is based on the capacity of the zirconium oxide to remove sodium. The zirconium oxide functions to remove sodium due to its high pH. On the other hand, one of the disadvantages of this structure as compared to the other resin beds (30 and 70) is that a high pH is required so that as the solution exits the second layer 86 it is at a higher pH.

Generally, it should be noted that preferably the resin beds of the present invention are structured so that urea is removed in either the first or second layers. Then preferably sodium is removed. After the sodium is removed, ammonium and then phosphate is removed. Additionally, the zirconium oxide layer functions to control the pH of the solution exiting the resin bed.

As previously noted, the resin bed of the cartridge can comprise any number of layers greater than four. It should also be noted that the layers may not have discrete boundaries, but, may be blended together. For example, it is possible to have a gradient of two materials between the zirconium oxide and the zirconium phosphate layers.

By way of example, and not limitation, real-time values for solute concentration at the inlet and outlet of cartridge 32 of the present invention will now be set forth. Due to mixing and mass transfer effects, these concentrations will be different at other locations of the system.

| Parameter | Input value | Output value |
|---|---|---|
| Urea Concentration [mg/L] | 5-20 | <10% of input value |
| Creatinine concentration [ ] | 2 | <20% of input value |
| Phosphate concentration [ ] | | <20% of input value |
| Sodium concentration [mEq/L] | 122-142 | 122-142 |
| Calcium concentration [mEq/L] | 2.5 | <0.2 |
| Magnesium concentration [mEq/L] | 0.5 | <0.05 |
| Ammonium concentration [ppm] | n.a. | <20 |
| Aluminum concentration [ppb] | n.a. | <10 |

Average Values

Preferably, the time-averaged concentration of the following parameters will be maintained within the given boundaries as measured in the cartridge effluent:

| | |
|---|---|
| PH | 7.0-7.4 |
| Sodium [mEq/L] | 127-137 |
| Chloride [mEq/L] | 85-98 |
| Bicarbonate [mEq/L] | 25-35 |

The pH of the effluent from the cartridge will be maintained between 6.5 and 8.0 at all times Net Solute Removal/Addition

| Parameter | Amount Removed |
|---|---|
| Urea-nitrogen | 9.8 at an input concentration of 20 mg/dL |
| Creatinine | 1.44 g |
| Phosphate | 1.44 g |
| Sodium | 20-60 mEq |
| Bicarbonate | 20-60 mEq |

Note: The capacity to process urea, creatinine, or phosphate depends upon the input concentration of that component. The capacity for a given component is defined by the component breakthrough, which is the amount absorbed by the cartridge when the effluent concentration exceeds a prescribed level (i.e., 10% of the input value). For safety reasons, Ammonium breakthrough levels are defined in absolute terms at 20 ppm.

As noted above, a variety of different layer structures for the resin bed are possible within the cartridge 32. In constructing the cartridge 32, the processes occurring in the cartridge must be considered. While the cartridge performs its primary task of removing urea, creatinine, phosphate, and other toxins, the by-products of this process result in changes in dialysate composition in three important respects: 1) sodium; 2) pH; and 3) bicarbonate. These three parameters are intimately related.

Sodium can be affected by three distinct processes within the cartridge:

1) Release of sodium in exchange for ammonium and other cations (calcium, magnesium, potassium). The maximum quantity of these cations to be absorbed will be about 650 mmol, consisting of about 430 mmol of ammonium and about 200 mmol of the other cations. The amount of sodium released during this exchange process is dependent on the equilibrated pH of the zirconium phosphate, the solution pH, and the concentration of cations in the dialysate.

2) pH equilibration of zirconium phosphate. In this process, sodium is exchanged for hydrogen ion in response to a solution pH which is different from the equilibrated pH of the resin. This exchange can occur in either direction, depending on whether the solution pH is above or below the equilibrated pH. It is expected that the solution pH will be greater than the equilibrated pH of the resin for much of the therapy, resulting in a net adsorption of $Na^+$ from solution.

3) Ion exchange of zirconium oxide. As an amphoteric resin, zirconium oxide is capable of removing sodium from solution if the equilibrium pH of the zirconium oxide is sufficiently basic.

4) Adsorption of sodium by the mixed bed (demineralization) resin, if present. The amount of sodium absorbed is entirely dependent on the quantity of mixed bed resin present.

5) Liberation of alkali upon conversion of urea. Conversion of urea is a continuous process throughout the therapy. Conversion of urea may contribute up to 430 mmol alkali, and is directly related to a patient's urea load.

6) Formation of bicarbonate during the conversion of urea. Formation of bicarbonate acidifies the solution, but this effect is partially offset by venting of carbon dioxide from solutions.

7) Venting of carbon dioxide from the cartridge loop. In solution, carbon dioxide acts as an acid. Thus, removal of carbon dioxide by its movement to the gas phase and subsequent venting out of the system results in a net loss of acid from solution.

8) Buffering of the solution by zirconium phosphate. It is expected that the solution pH will be greater than the equilibrated pH of the resin resulting in a net release of acid ($H^+$) to the solution.

9) Buffering of the solution by zirconium oxide. The zirconium oxide resin exchanges $H^+/OH^-$ if it is in contact with a solution having a pH different from its equilibrated pH.

Bicarbonate levels can be affected by three distinct processes within the cartridge:

1) Formation of bicarbonate during the conversion of urea. One mole of carbon dioxide/bicarbonate is formed from each mole of urea. Dissolved carbon dioxide is in equilibrium with bicarbonate according to the following relation:

$$pH = 6.2 + \log \frac{HCO_3^-}{CO_2(aq)}$$

Consequently, the ratio of carbon dioxide/bicarbonate formed as a result of the urease reaction is dependent on the solution pH, with more acidic conditions favoring carbon dioxide. The overall quantity of (carbon dioxide+bicarbonate) formed is dependent on the patient's urea load.

2) Venting of $CO_2$ from the cartridge loop. Dissolved carbon dioxide is in equilibrium with the partial pressure of carbon dioxide in the gas phase. Thus, carbon dioxide will bubble out of solution if the solution partial pressure exceeds the partial pressure of the gas phase.

3) Adsorption of bicarbonate by zirconium oxide. zirconium oxide resin in the hydroxyl form is capable of adsorbing bicarbonate. Conversely, zirconium oxide resin in the bicarbonate form is capable of releasing bicarbonate into the solution.

The possible manipulations within the cartridge that can be made are as follows:

1) Altering the equilibrated pH of the zirconium phosphate resin. By lowering the equilibrated pH of the resin, the amount of sodium released is reduced, the average dialysate pH is lower, and the amount of carbon dioxide formed is greater. By raising the equilibrated pH of the resin, the solution pH becomes more physiologic, but the amount of sodium and bicarbonate released is increased.

2) Altering the equilibrated pH of the zirconium oxide resin or loading the resin with various counter-ions. Hydroxyl-loaded zirconium oxide results in a more physiologic solution pH, adsorption of bicarbonate from solution and increased adsorption of cations.

By way of example and not limitation, the experiments below set forth further embodiments and analysis of the invention.

Experiment No. 1

Set forth below are tests that examined the effect of modifying the equilibrium pH of zirconium phosphate on the composition of the dialysate effluent. The primary endpoints observed were pH, sodium concentration, and bicarbonate concentration. The ideal result is an effluent pH at or near the physiologic pH of 7.4, a net sodium removal of ~50 mEq for a full-sized cartridge, and a net bicarbonate addition of ~50 mEq for a full-size cartridge. These experiments were typically conducted at a g scale of zirconium phosphate, in a manner such that the urea concentration at ammonium breakthrough is in the expected column input range during patient therapy. At this scale, appropriate performance targets are a net sodium removal of ~1 mEq and a net bicarbonate addition of ~1 mEq (or 0.5 mEq/L for a 2 liter reservoir).

The resin was modified with phosphate buffer to increase the effluent pH by the following procedure. A large reservoir of 15 mM phosphate buffer was prepared using 10.8 mM dibasic sodium phosphate, 4.2 mM of monobasic sodium phosphate and 117 mM sodium chloride. The buffer was pumped through a column of resin in single pass mode. The flow rate was scaled to achieve a residence time of ~5 minutes. The effluent pH was monitored closely, and the experiment was stopped when the effluent pH reached the desired value.

With this technique the action can be modified up to a pH of 7.2. For higher pH the same phosphate buffer is prepared and 0.1 M NaOH is added to raise the pH to the desired value.

For the modified zirconium phosphate materials, static tests were performed to determine the equilibrium capacity for ammonium. The equilibrium isotherms for the different materials are not significantly different from one another over the working concentration range [3-15 mM].

Tests were performed using a 2-liter bag as a reservoir with recirculation through columns containing the material. The bag was maintained at a uniform concentration with the aid of a shaker. The solution was pumped through the column(s) and returned to the solution bag. The bag has an outlet port with an injection site, and an inlet port that is extended 9.5 inches into the bag. The extension of the inlet port into the bag minimizes channeling between the two ports and ensures proper mixing. The solution used in these tests was Dianeal PD4 (1.5% glucose) spiked with urea and bicarbonate. precautions were taken during the filling and sampling procedures to ensure that the integrity of the system was maintained.

All the tests were performed using a urea concentration of 10 mg/dL and a sodium bicarbonate concentration of 25 mM. The initial pH for this solution was 7.4.+−.0.2. For all the tests, 10 grams of cation material were used. Two types of urease were employed in these tests, CLEC-urease from Altus Biologics (5-20 mg) and urease from Sorb Technologies (5 g mixed with 10 g alumina). For the Sorb urease a 25 mL column was used with 8 μm filters on both ends. The urease alumina mixture was sandwiched between two lays of alumina (~5 g each). The Sorbtech urease was packed dry. The CLEC-urease was packed wet, sandwiched between layers of Sephacryl (inert chromatography media from Sigma Chemicals) in a 10 ml column. No difference in performance was observed between the two forms of urease.

Prior to the experiment the urease was flushed with Dianeal to remove any labile or very small particle size enzyme. After the pump was started, time zero was defined by the appearance of fluid exiting the column outlet port. Samples were collected over time from both the inlet and outlet to the two-liter bag, and analyzed immediately for sodium, pH and bicarbonate using a blood gas analyzer (Chiron model 860, Chiba Corning).

Table 4 shows a summary of the relevant tests performed. Additional experiments were performed using a phosphate buffer.

From these tests it is apparent that the change in pH during the test is reduced when the pH of the resin is modified to a higher (than 6.2) pH. With an increase in resin pH the performance of the resin in terms of ammonia adsorption maintains the same, but more sodium is released into the system. The presence of the urease works in reducing the changes in pH.

TABLE 4

Results of small-scale test using urease and zirconium phosphate

| Resin pH | Date | Solution pH, initial | Solution pH, final | ΔpH | ΔNa⁺ (mEq) | NH₄⁺ bound (mEq) | ΔHCO3 (mmol/L) |
|---|---|---|---|---|---|---|---|
| 6.2 | Apr. 21, 2000 | 7.80 | 7.13 | −0.67 | 0.5 | 7.3 | 0.5 |
| 6.8 | May 4, 2000 | 7.41 | 7.21 | −0.20 | 3.8 | 8.6 | 2.5 |
| 7.1 | Apr. 21, 2000 | 7.25 | 7.47 | +0.22 | 5.5 | 5.9 | 4.4 |
| 7.4 | May 4, 2000 | 7.45 | 7.59 | +0.14 | 5.1 | 6.5 | 2.9 |
| 7.4 | May 15, 2000 | 7.38 | 7.46 | +0.08 | 4.9 | 6.9 | 1.7 |

TABLE 4-continued

Results of small-scale test using urease and zirconium phosphate

| Resin pH | Date | Solution pH, initial | Solution pH, final | ΔpH | ΔNa$^+$ (mEq) | NH4$^+$ bound (mEq) | ΔHCO3 (mmol/L) |
|---|---|---|---|---|---|---|---|
| 7.6 | May 6, 2000 | 7.44 | 7.47 | +0.03 | 5.5 | 8.8 | 5.3 |
| 7.6 | May 15, 2000 | 7.36 | 7.56 | +0.20 | 4.1 | 7.3 | 3.2 |

Experiment No. 2

Figure 8:
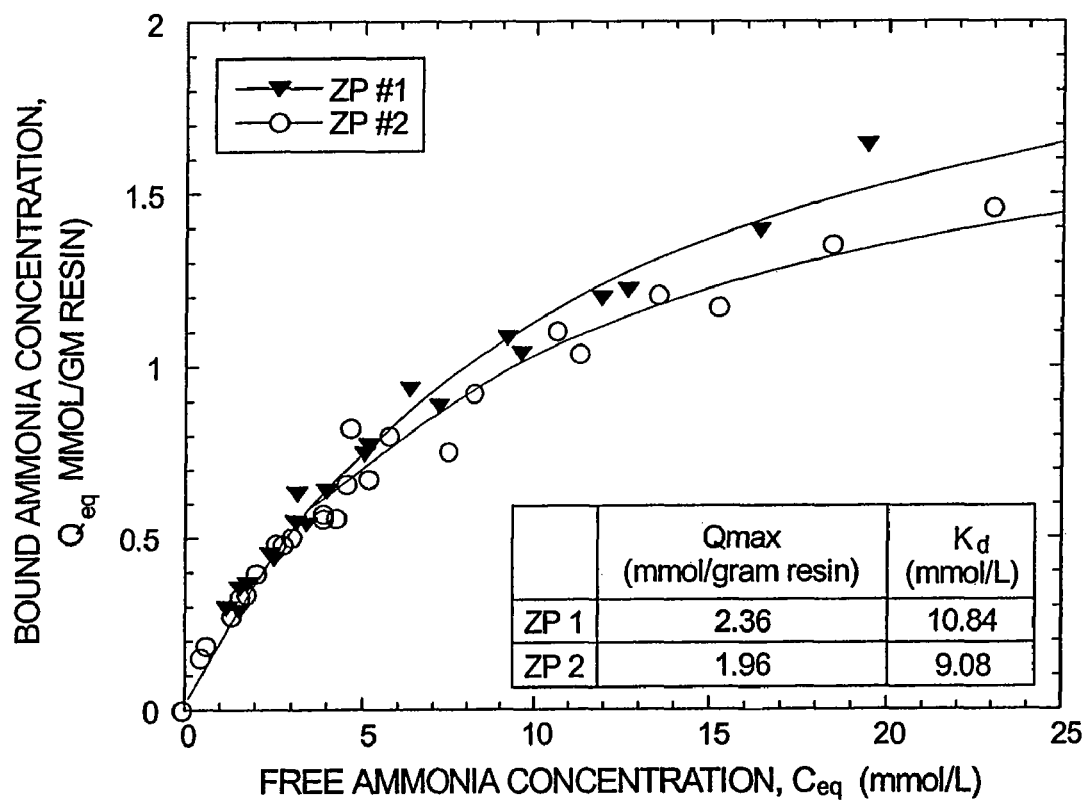
FIGS. 8-10 illustrate graphically the results of Experiment No. 2.
Figure 9:
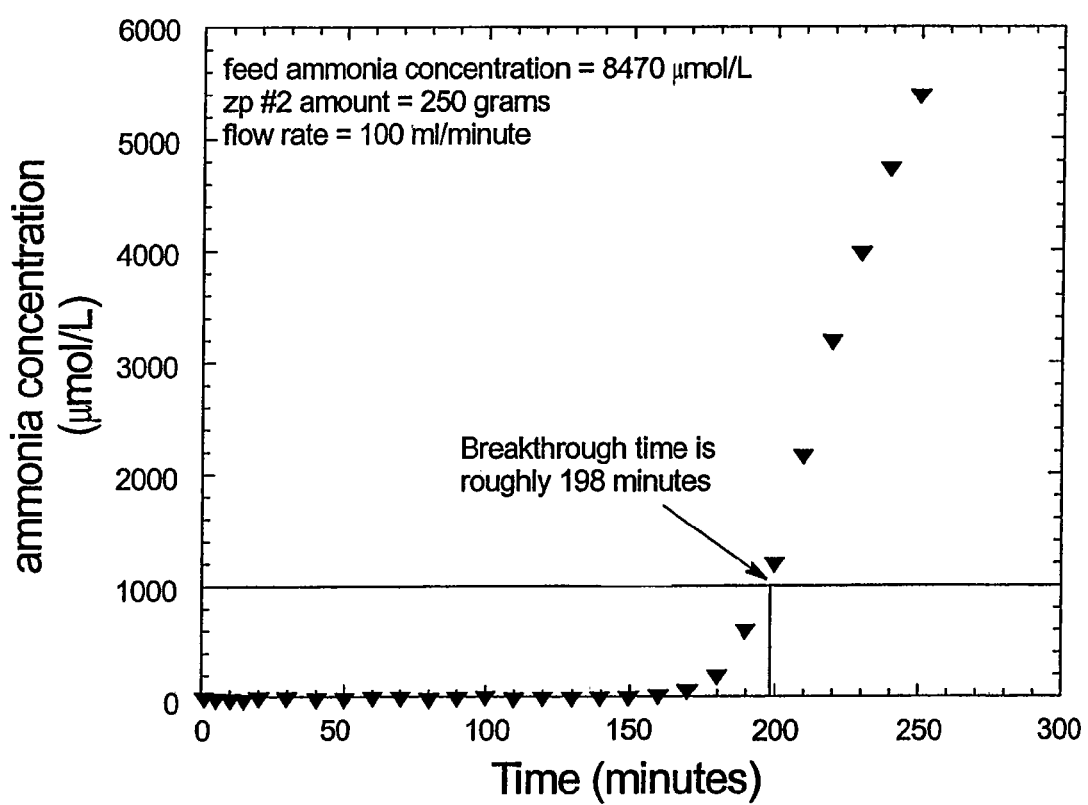

Experiments were conducted using urease, zirconium phosphate, and zirconium oxide in the same experimental set-up as above. Multiple columns were connected in series, with the zirconium oxide column added to the system after the cation column. The results for a test using Altus 271-6 urease, zirconium phosphate modified to a pH of 7.2 and zirconium oxide are set forth below in FIGS. 8-10. Note that the sodium balance is well maintained over the course of the test, which is a result of zirconium oxide removing sodium from the solution to counterbalance sodium released by the zirconium phosphate layer. Effluent pCO$_2$ levels are also significantly lower in the presence of zirconium oxide. Modified zirconium oxide captures sodium, and helps maintain the sodium balance over the course of the test. The test show that zirconium phosphate modified to a pH of 7.1-7.2 performs much better than those modified to a higher pH.

Experiment No. 3

Experimental Setup

Figure 11:
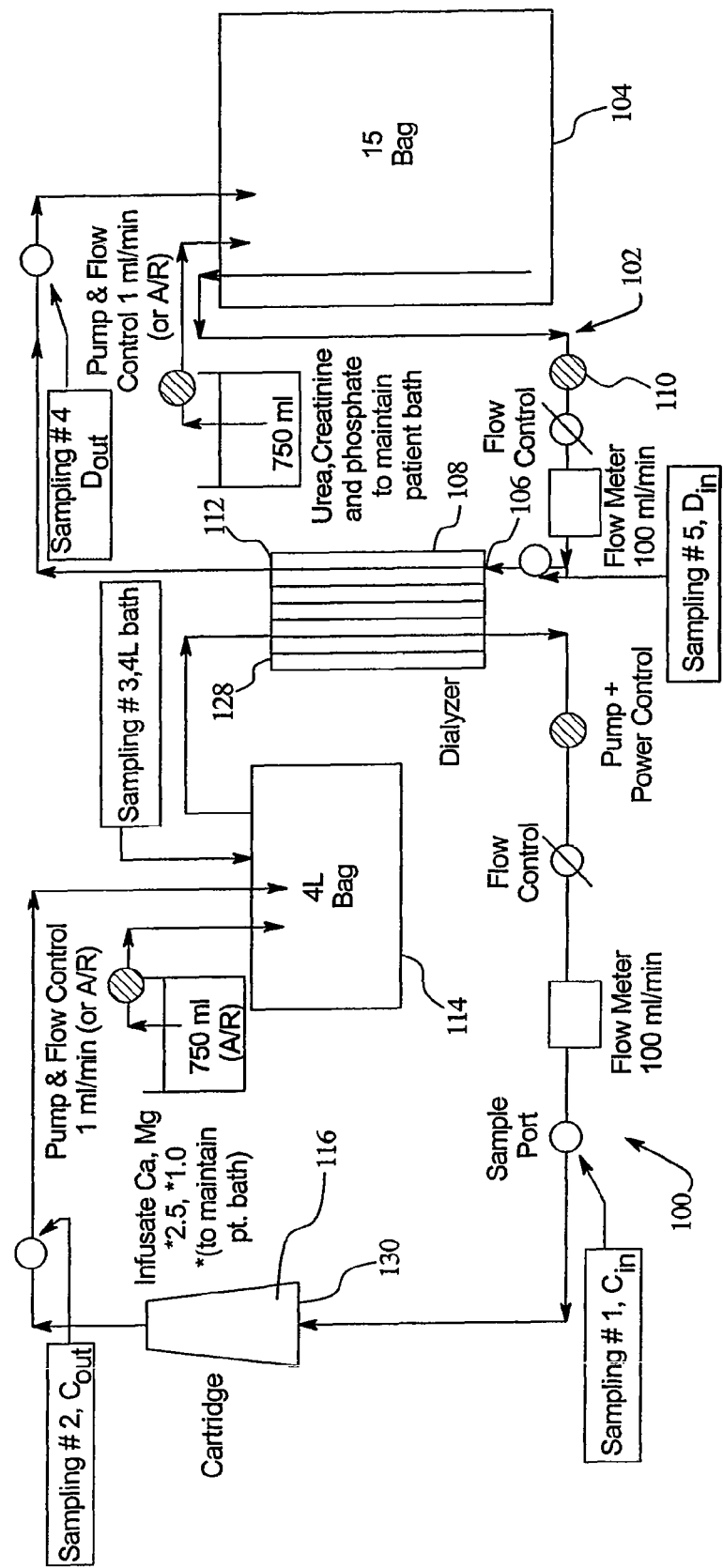
FIG. 11 illustrates the system that was used in Experiment No. 3 for testing the cartridges of the present invention.

FIG. 11 illustrates a schematic of the experimental setup used in a study to evaluate the use of ion exchange resins in peritoneal dialysis setting. The set up included two loops 100 and 102. A 15-liter bag 104 representing the total fluid body of a patient was used in the second loop 102 of the setup. Although utilizing a 40-liter bag may make a more accurate estimation of the patient body, a 15-liter bag was used due to ease of analysis. The fluid from the 15-liter bag was pumped into the lumen side 106 of the dialyzer 108 at a flow rate of 100 mL/min using a pump 110. From the outlet 112 of the lumen side 106 of the dialyzer 108, the fluid returned to the 15-liter bag 104. Concurrently, as this fluid was returning into the 15-liter bag 104, it was infused with urea, creatinine, and phosphate, at 1 mL/min, to represent the total amount of wastes being generated continuously by the patient. The 15-liter bag 102 was maintained at a constant concentration of urea-nitrogen (20 mg/dL), creatinine (6 mg/dL), and phosphate (3.1 mg/dL). The initial feed solution contains 25 mmol/L of bicarbonate, 138 mEq/L of sodium, 2.5 mEq/L of calcium and 1.0 mEq/L of magnesium.

A 4-liter bag 114 containing sodium at 132 mEq/L, calcium at 2.5 mEq/L, magnesium at 1.0 mEq/L and bicarbonate at 25 mmol/L in DI water is provided. Initially the 4-liter solution is used to prime the dialyzer 108 and a cartridge 116. As the solution exits the cartridge 116, all the toxins and also calcium and magnesium, are completely removed. Accordingly, fluid returning to the 4-liter bag 114, is infused with calcium and magnesium so as to maintain the calcium and magnesium balance in the 15-liter bag 114. Both the 4-liter 124 and the 15-liter 114 bag were well mixed and the dialyzer 118 was operated at close to zero ultra filtration.

From the 4 L bag 114, the solution flows into the shell side 128 of the dialyzer 108. The urea creatinine and phosphate diffuses from the lumen side 116 of the dialyzer 108 to the shell side 128. The solution that exits the dialyzer 108 and enters the cartridge 116 has a urea nitrogen concentration of 10 mg/dL, Creatinine concentration of 3 mg/dL and phosphate 1 mg/dL. The flowrate on either side of the dialyzer 38 is maintained at 100 ml/mm.

The cartridge 116 was constructed as set forth above. Urea creatinine and phosphate flows to the bottom 130 of the cartridge 116, which contains urease, various ion exchange resins, and carbon. As noted above, urease is an enzyme whose function is to convert toxic urea into ammonium and carbon dioxide, is the first layer in the cartridge. The middle layer comprises of two different types of ion exchange resins, zirconium phosphate (zirconium phosphate) and zirconium oxide (zirconium oxide). Zirconium phosphate, as noted above, mainly removes ammonium ions, calcium, and magnesium from the solution, while releasing hydrogen and sodium. The zirconium oxide resin removes the phosphate. Finally, a carbon layer is used to remove creatinine, uric acid, and other organics from the solution. From the top of the cartridge, fluid is then directed back into the original 4-liter bag 114.

Pursuant to this study, samples were taken at 5 different points in the above setup. Sample "1" ($C_{IN}$) was taken before the fluid enters the cartridge inlet; Sample "2" ($C_{OUT}$) was taken as the sample exits after the cartridge; Sample "3" (4 L) was taken directly from the outflow of the 4-liter bag; Sample "4" ($D_{OUT}$) was taken as the fluid comes out of the lumen of the dialyzer; Sample "5" ($D_{IN}$) represents the fluid before entering the lumen inlet of the dialyzer. The sample $D_{IN}$ was taken from the 15 L bag 34, which is essentially well mixed and represents 15 L patient.

Figure 12C:
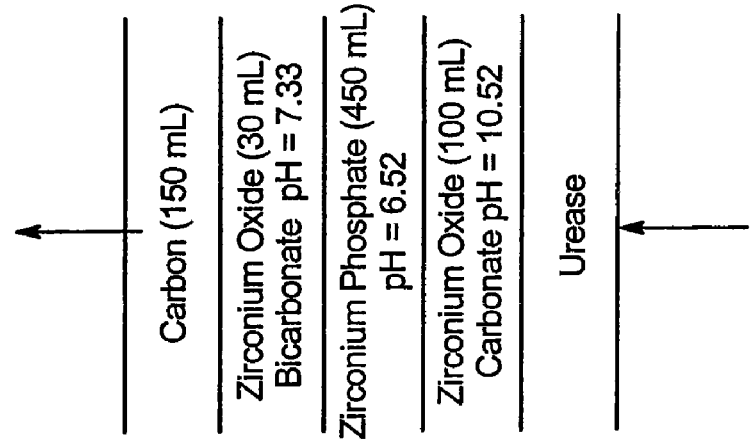
FIGS. 12a-c illustrates a cross-sectional view of the layers of the cartridge used in Experiment No. 3.
Figure 12B:
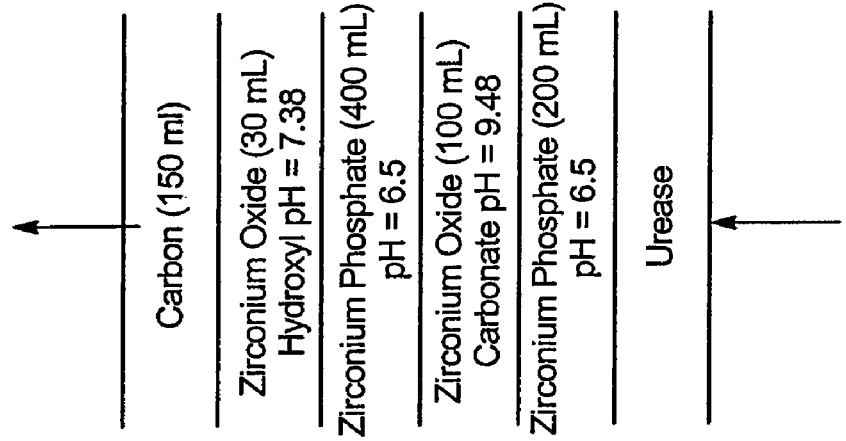
Figure 12A:
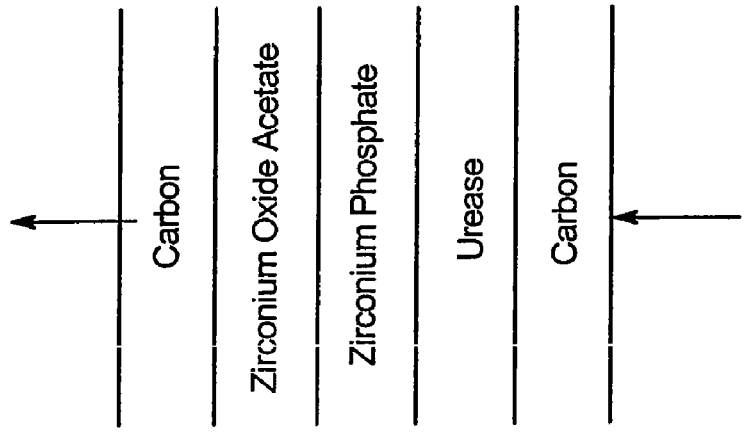
Figure 13A:
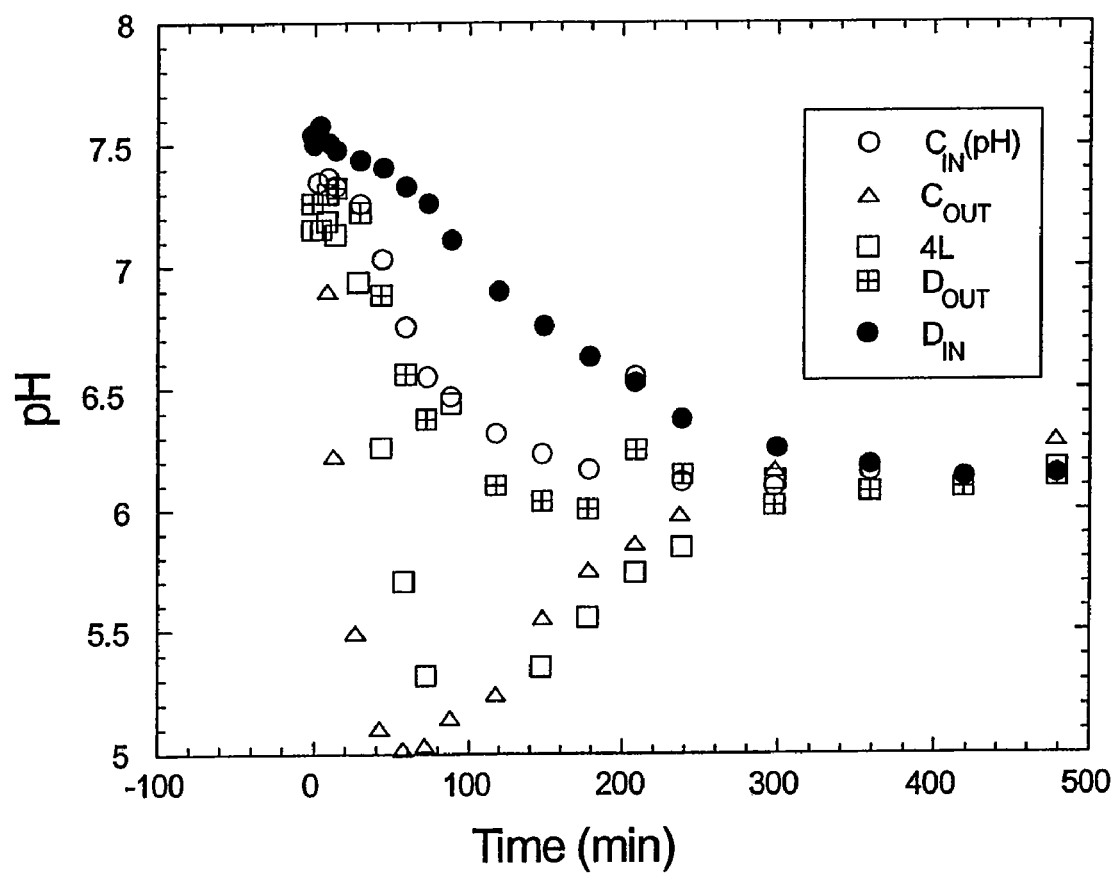
FIGS. 13a-c illustrate pH, sodium bicarbonate profiles of samples taken pursuant to Experiment No. 1.
Figure 13B:
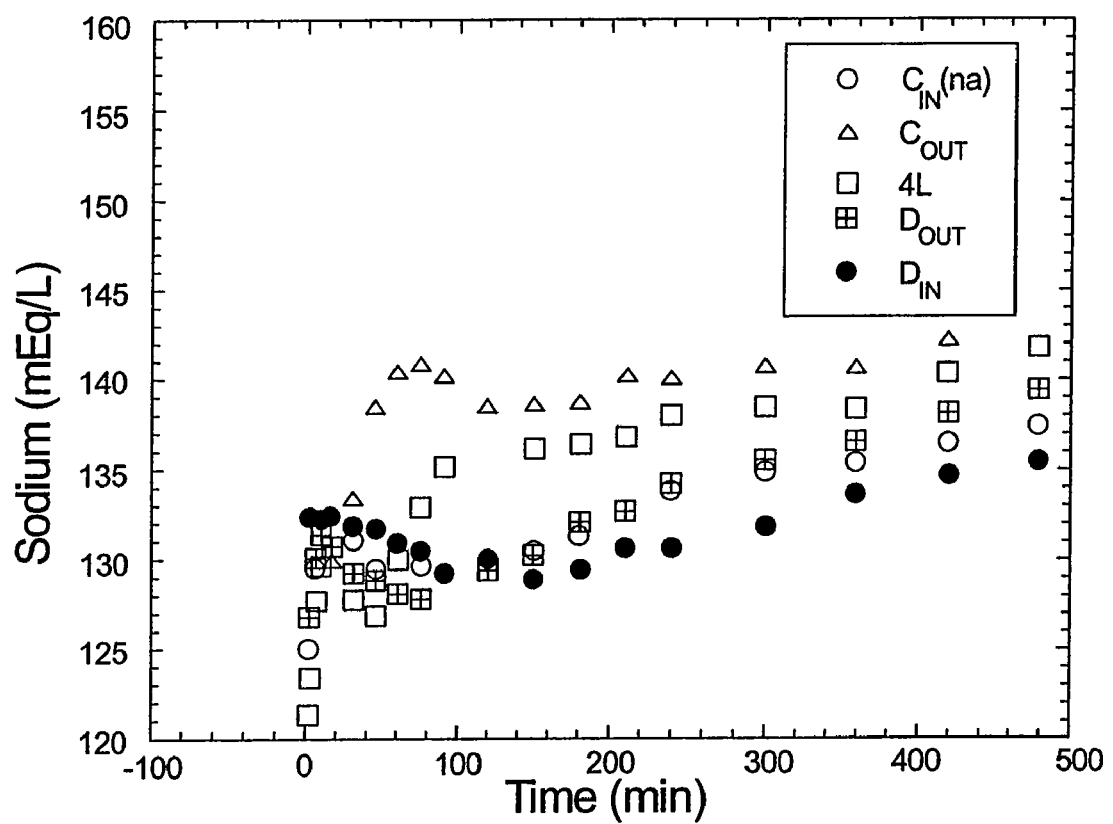
Figure 13C:
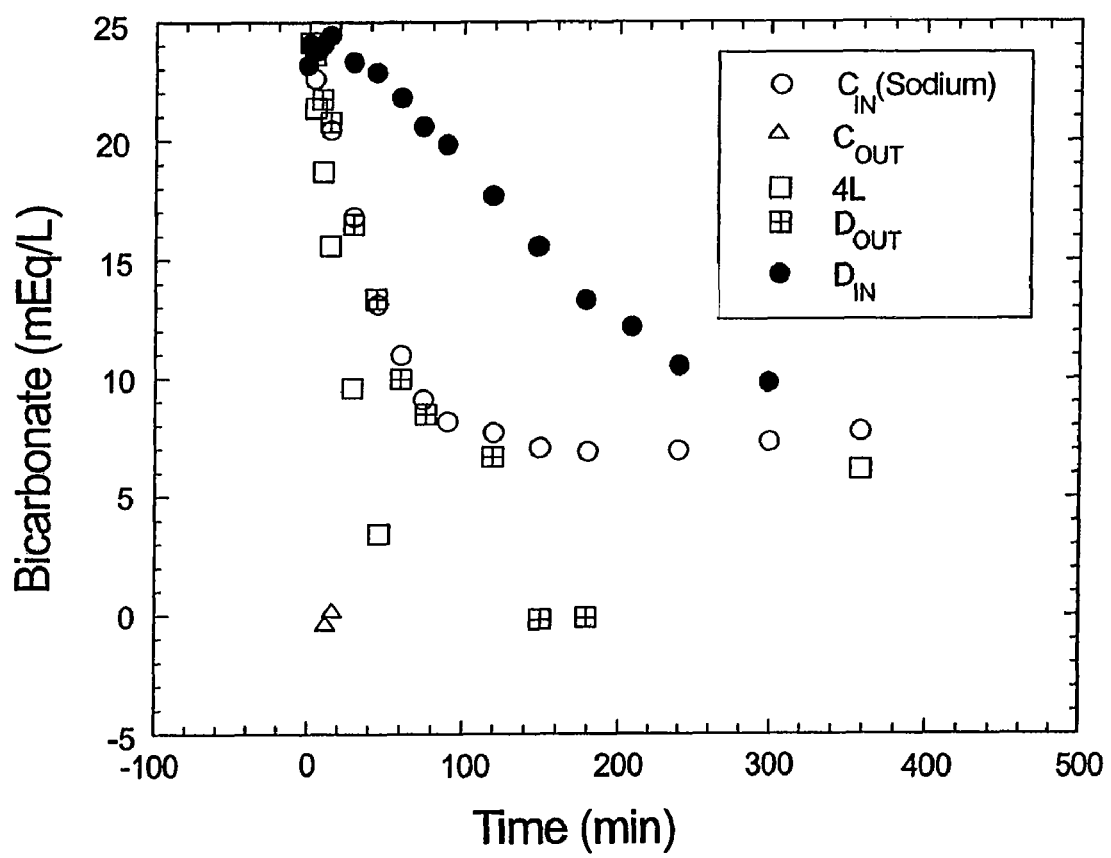

The above experimental setup was used to evaluate an embodiment of the cartridge of the present invention. A Redy Cartridge was obtained from Sorb Technology and used in the above experimental setup. FIG. 12 shows the various layers in the cartridge. FIG. 12a represents the Redy Cartridge, FIG. 12b represents the Redy Cartridge 1 and FIG. 12c represents the Redy Cartridge 2. The urea, creatinine and phosphate diffuse from 15 L patient bag across the dialyzer to the bottom of the cartridge. Five samples were taken from various locations as shown in FIG. 11. Samples were analyzed for pH, bicarbonate and sodium onsite. Analysis for urea, creatinine, phosphate, calcium, magnesium, chloride, lactate, and glucose were also carried out. FIGS. 13a, 13b, 13c show the pH, sodium and bicarbonate profiles. The pH in the 15 L patient bath drops from 7.546 to 6.156, bicarbonate drops from 23.2 to 0.0, sodium increases from 132.4 mEq to 135.3 mEq.

Instead of providing bicarbonate to the patient, bicarbonate is removed and sodium added. Also the pH drops and PCO2 increases. Table 4 summarizes the pH, sodium, and bicarbonate profile from this study. Overall, 44 mEq of sodium was added and all of the bicarbonate was removed. This was a net gain of 125 mEq of sodium. The cartridge does remove urea, creatinine and phosphate completely, but does not satisfy the electrolyte requirement. Thus the resins or the cartridge cannot be used in peritoneal dialysis closed loop setting or in hemodialysis applications, it cannot be used unattended. Several different combinations were evaluated that could satisfy the requirement criteria for use in the cartridge for continuous recirculation of peritoneal dialysis solution. Some of the combinations were as follows:

1—Zirconium oxide in bicarbonate form at a pH of 8.85 used with zirconium phosphate (pH=6.2) in its standard form. In this setup there were only 4 layers.

2—Zirconium phosphate with a pH of 6.5 along with zirconium oxide in the bicarbonate form at two different pHs of 10.52 and 7.33. At the higher pH, bicarbonate should be in the form of carbonate.

3—Zirconium phosphate at a pH of 6.5 was used the bicarbonate form of zirconium oxide at a pH of 9.35 and 9.83 and the hydroxyl form of the zirconium oxide at a pH of 7.14 and 7.23.

4—Zirconium phosphate at a pH of 6.49 used along with zirconium oxide in the bicarbonate form at a pH of 8.80. In this case also there were 4 layers.

5—Since zirconium oxide is an amphoteric resin, this resin needs to adsorb the $Ca^{++}$ and $Mg^{++}$ ions, allowing the reduction of zirconium phosphate volume to 450 ml.

FIGS. 12b and 12c represents two alternatives from the various alternatives discussed.

FIG. 12b and FIG. 12c shows the modified cartridge in the study. From equilibrium adsorption isotherm studies it was shown that at a concentration of 10 mg/dl urea nitrogen in the peritoneal dialysis solution a 600 ml resin column is required. Therefore the size of the resin in Cartridge I (FIG. 6b) is 600 ml. In FIG. 2b, (cartridge I) the $1^{st}$ layer is urease, $2^{nd}$ layer is zirconium phosphate (pH=6.5, volume=200 mL), $3^{rd}$ layer is zirconium oxide in carbonate form (pH=9.48, volume=100 mL), $4^{th}$ layer is zirconium phosphate (pH=6.5, volume=400 mL) and $5^{th}$ layer is Zirconium oxide in the hydroxyl form (pH=7.38, volume=30 mL) the last layer is carbon. The zirconium oxide $3^{rd}$ (High pH) is used not only to adsorb the cations, but it can also raise the pH of the zirconium phosphate resin. The counter ions used in this resin could be bicarbonate, carbonate or hydroxyl. This layer adsorbs the calcium, magnesium, thus reducing the size of the zirconium phosphate layer as it is used only to adsorb ammonia. Phosphate is also adsorbed in this layer along with the other cations. The $5^{th}$ layer is zirconium oxide (pH=7.38) is used to adsorb phosphate and some sodium. But if there is no leaching of phosphate from the zirconium phosphate resin, this layer will not be required. The last layer is carbon, which again, can be placed anywhere.

Figure 14A:
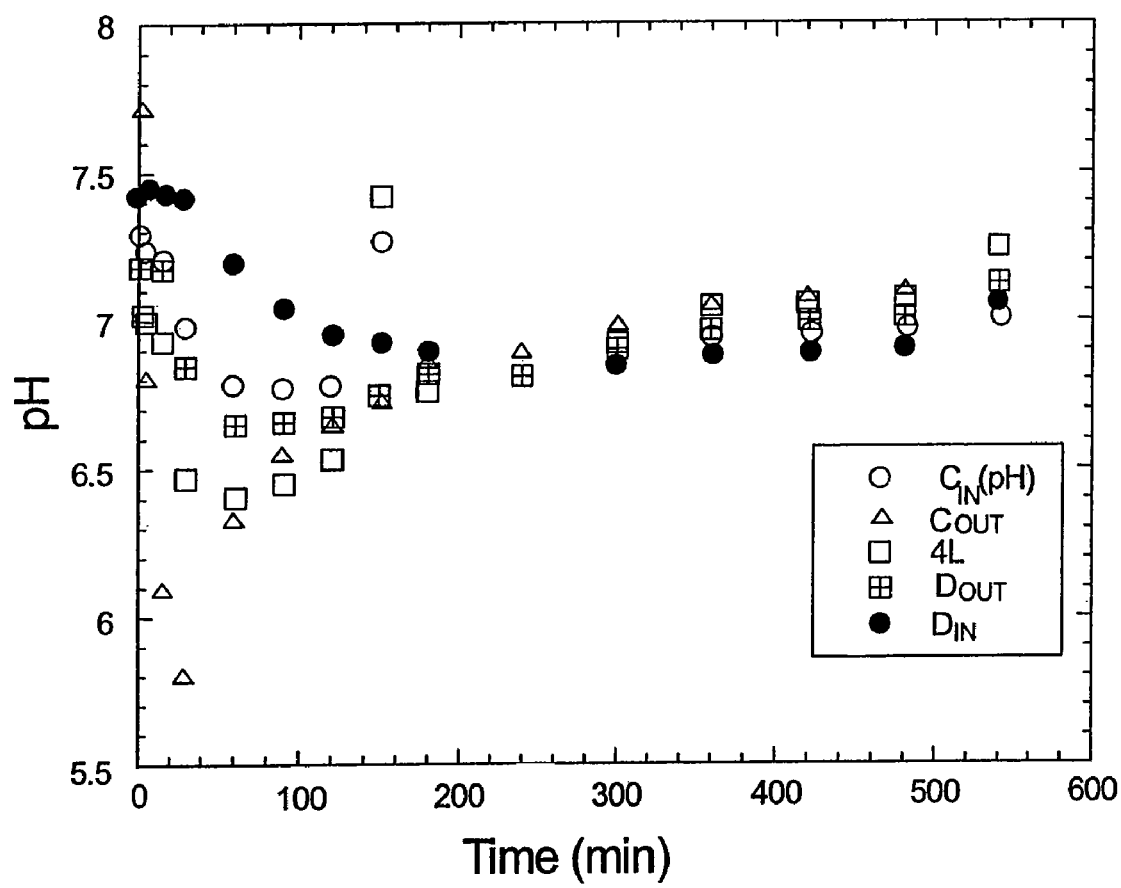
FIGS. 14a-d represent pH, sodium bicarbonate profiles of samples taken pursuant to Experiment No. 1.
Figure 14B:
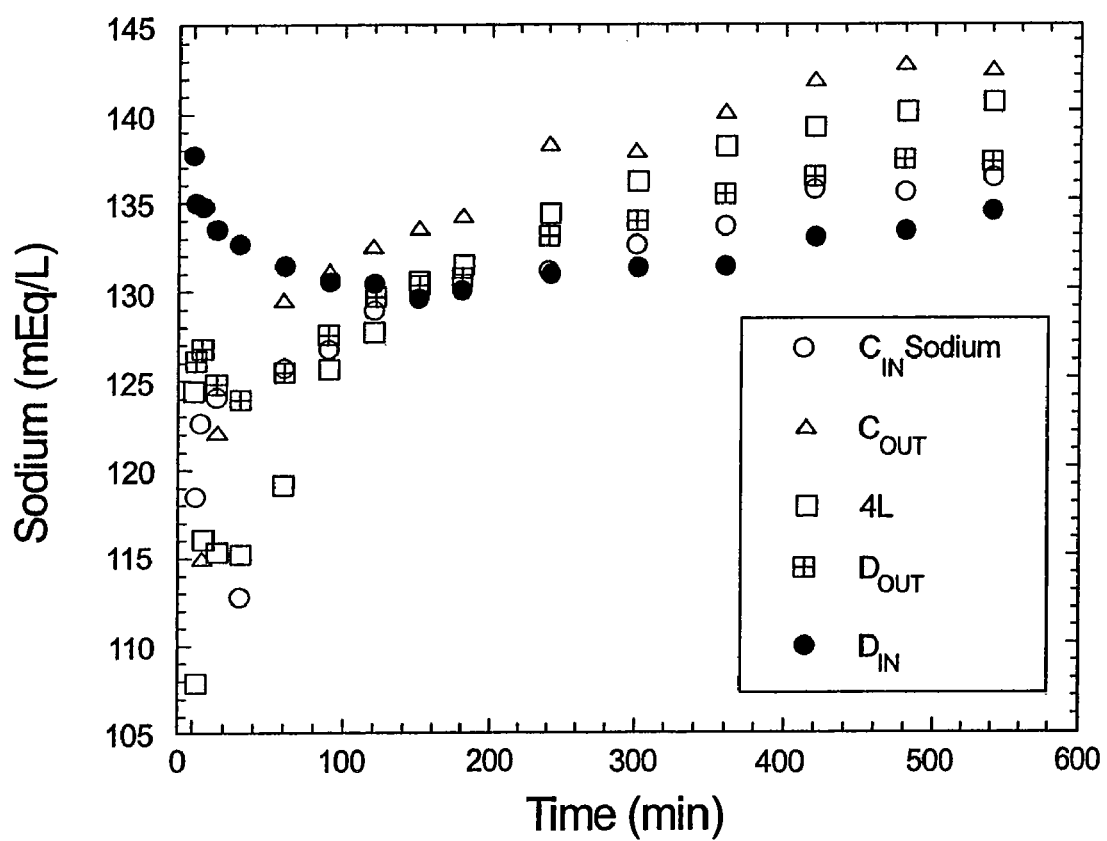
Figure 14C:
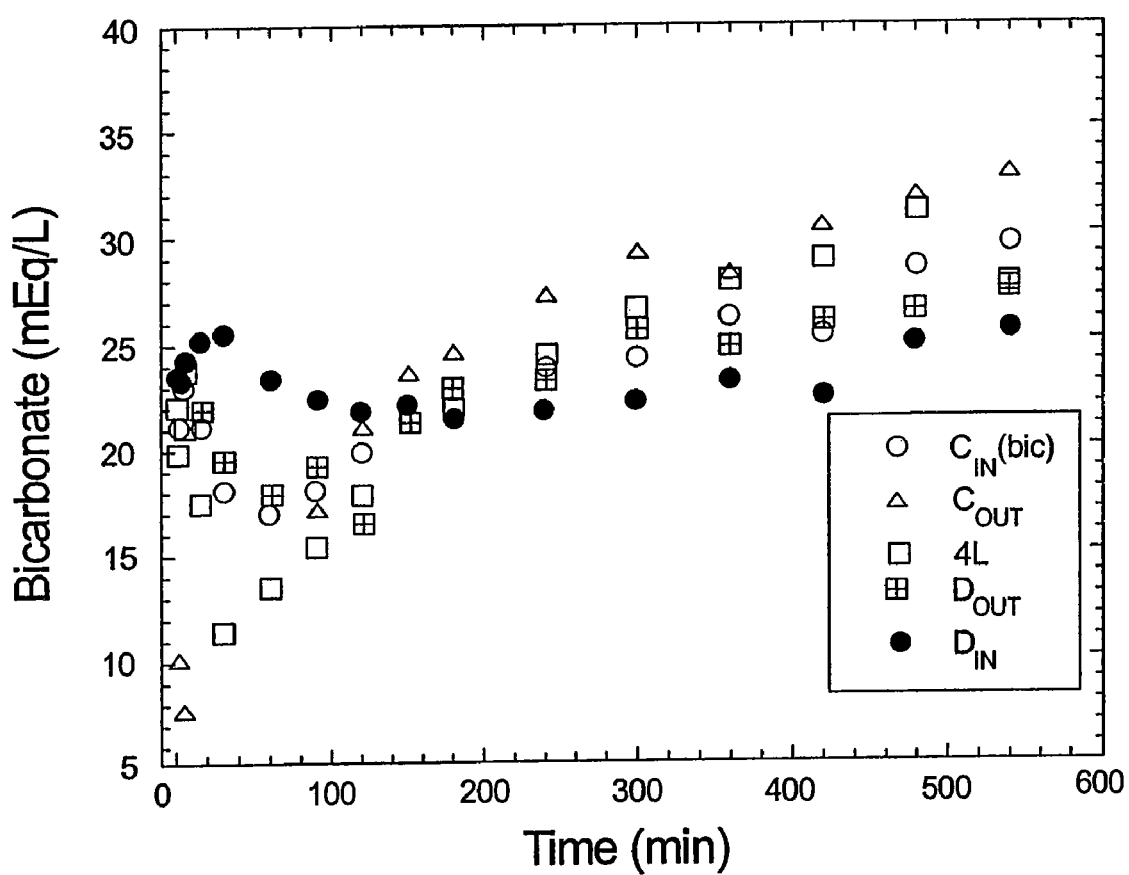
Figure 14D:
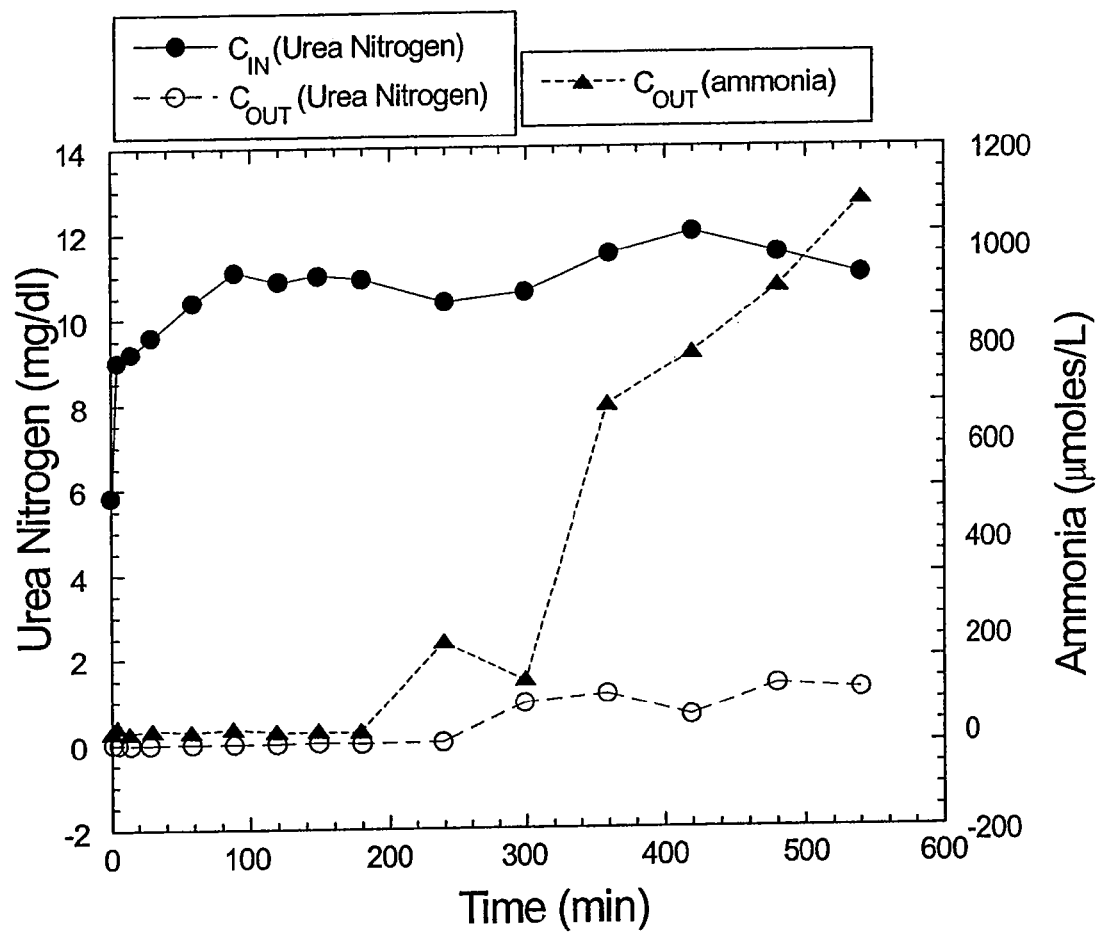

FIGS. 14a, 14b 14 c & 14d represent the pH, sodium bicarbonate and profile over the entire therapy time. Table 5 summarizes the pH, bicarbonate and sodium profile. The pH in the 15-liter patient bag goes from 7.49 to 6.9. Sodium is removed from the patient (15-liter bag) approximately 57 mEq is removed. The resins are designed such that it removes sodium initially for approximately 20 minutes or so, and then the cartridge slowly adds the sodium back. Similar trend is observed in the case of bicarbonate, also approximately 22.5 mEq of bicarbonate is added back to the 15-liter patient. In this experiment, as shown in FIG. 14d 4.94 gm of urea nitrogen is processed (10.6 gm of urea) which produces 353 mmol/L of ammonia and 176 mmol of bicarbonate. In the Redy cartridge run 124 mEq of sodium was added, but in our cartridge of the present invention only 5 mEq of sodium is added back into the circulation. In the cartridge of the present invention, the net bicarbonate gain was approximately 59 mEq. But in the cartridge run bicarbonate was completely removed. The pH in the 15-liter patient loop went down to 6.15 and all the bicarbonate was removed.

Figure 10:
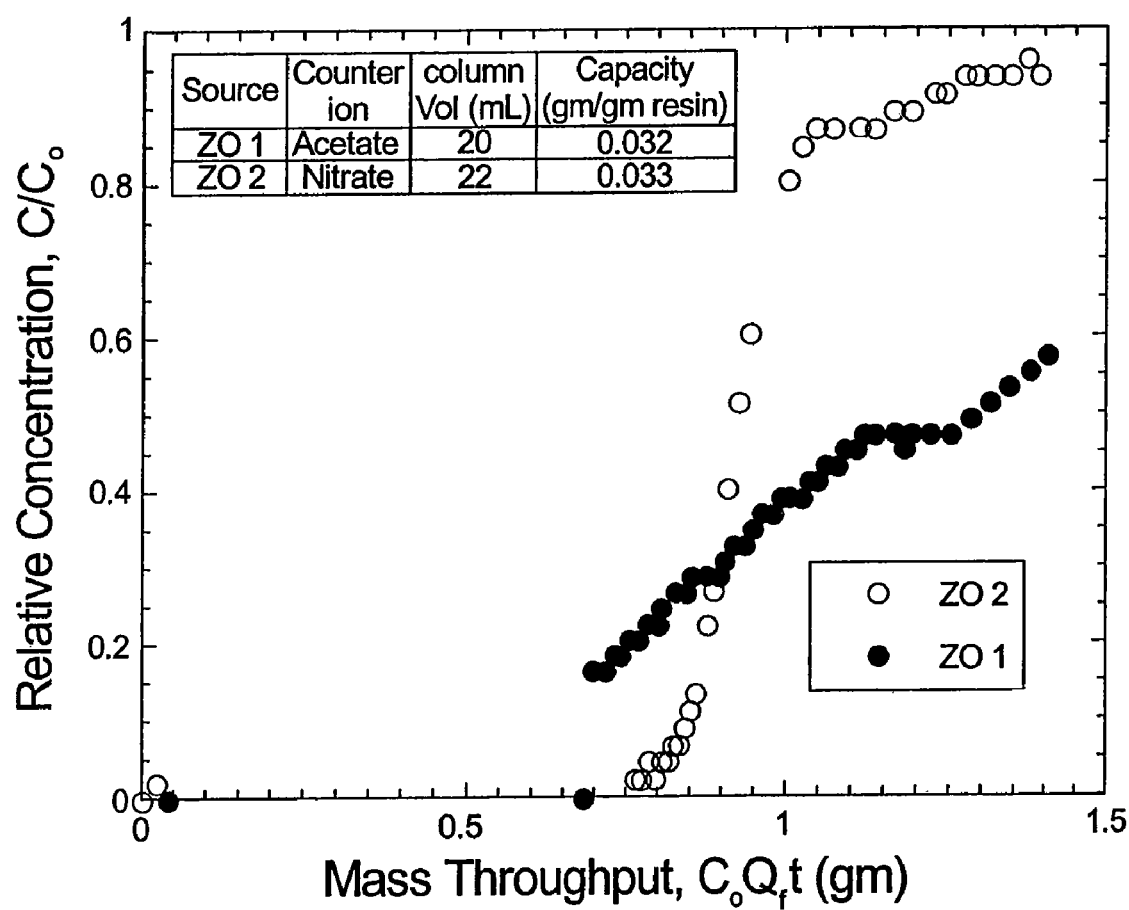

FIG. 12c shows the cartridge II used in the experimental setup described in FIG. 10. The amount of zirconium phosphate was reduced to 450 ml. Layers 2 and 4 were zirconium oxide in carbonate and bicarbonate form at pH of 10.52 and 7.33. Table 6 summarizes the results from this run. In this run, the pH of the zirconium oxide in layer 2 was higher so that it has better capacity for cations. Around 97.5 mEq of sodium was removed from the 15-liter patient bag and 15 mEq of bicarbonate was removed. There was net removal of 62 mEq of sodium. An addition of 5 mEq of bicarbonate in the stream. The bicarbonate profile can be improved in this run. Here we have also reduced the amount of zirconium phosphate to remove the same amount of urea.

Figure 15A:
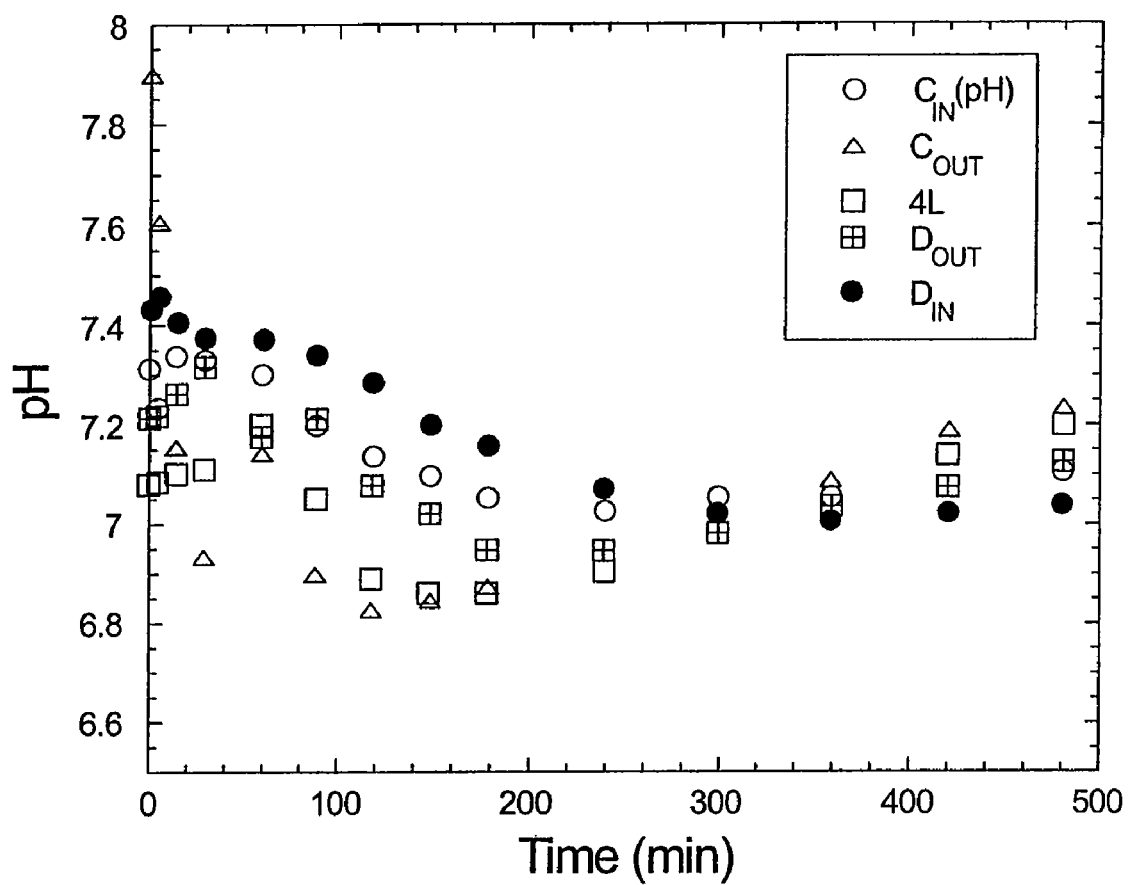
FIGS. 15a-c illustrate pH bicarbonate and sodium profiles of samples over time pursuant to Experiment No. 1.
Figure 15B:
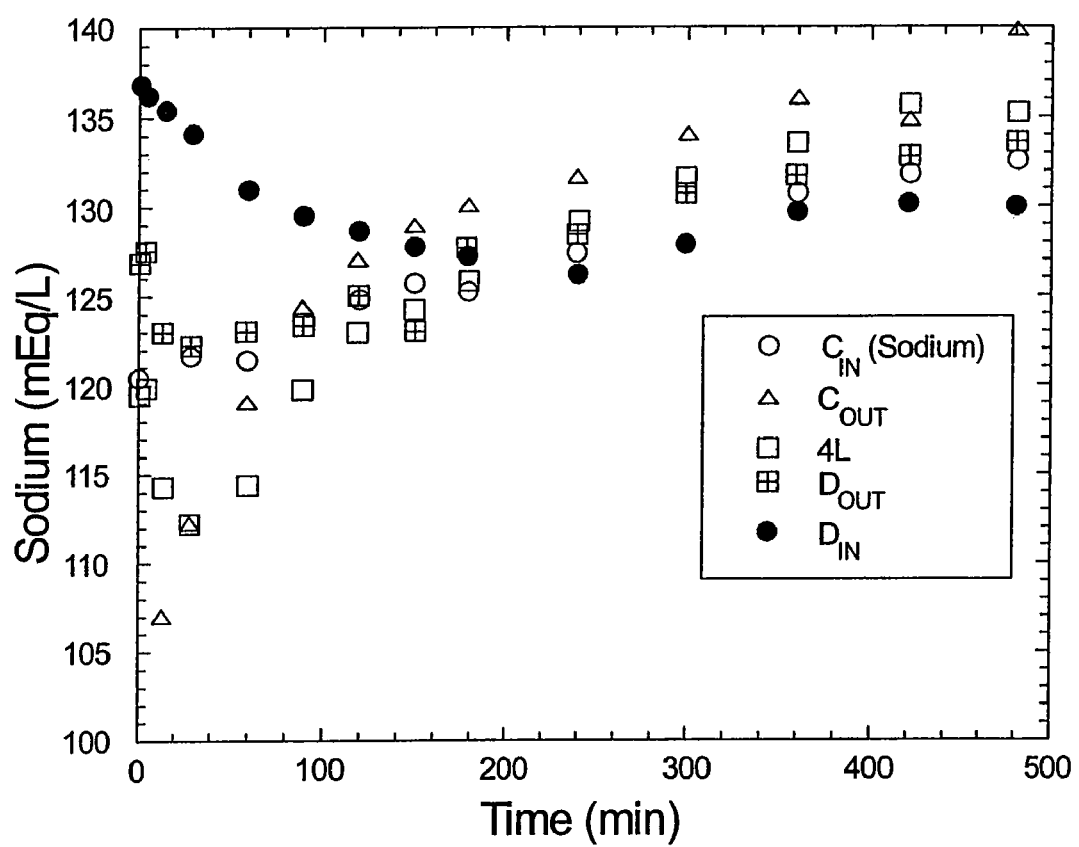
Figure 15C:
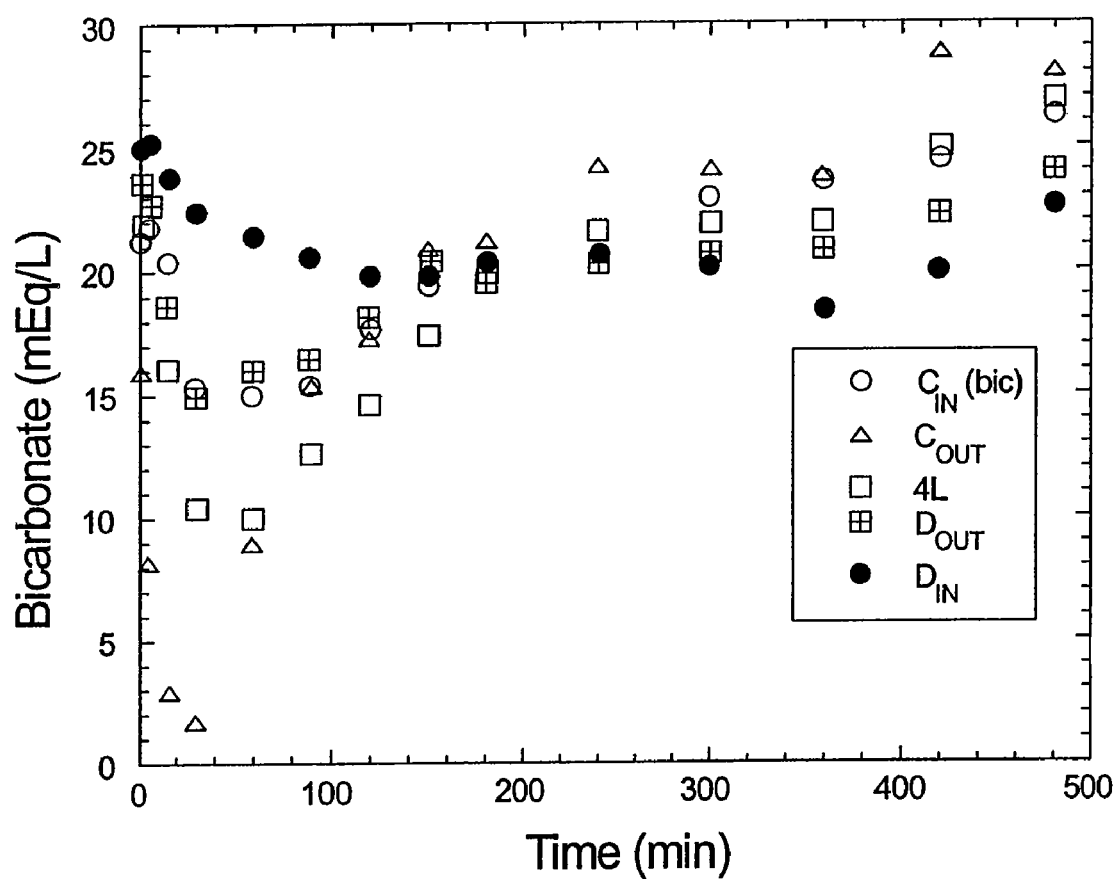
Figure 15D:
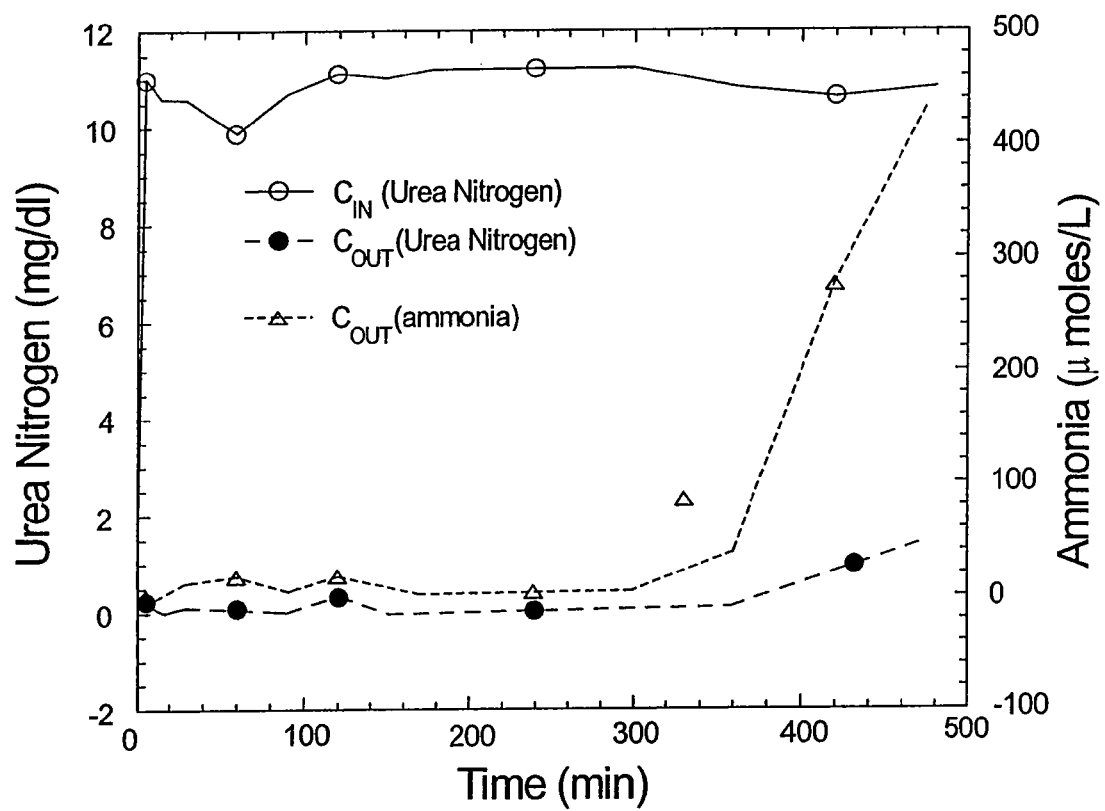
FIG. 15d illustrates the urea conversion over time pursuant to Experiment No. 1.

FIGS. 15a, 15b and 15c shows the pH bicarbonate and sodium profile over the entire therapy time. FIG. 15d shows the urea conversion. In this experiment a higher pH of the bicarbonate resin was utilized and also the zirconium phosphate resin was only 450 ml.

TABLE 5

Summary of Cartridge Test

| Time (Min.) | | Cartridge In | Cartridge Out | 4-Liter Bag | Gain/Loss 4-liter Bag (mEq) | 15-Liter In | 15-Liter Out | Gain/Loss 15-Liter Bag (mEq) |
|---|---|---|---|---|---|---|---|---|
| 0 | pH | — | — | 7.147 | — | 7.546 | — | — |
| 480 | pH | 6.153 | 6.3 | 6.17 | — | 6.14 | — | 6.156 |
| 0 | Sodium (mEq/L) | — | — | — | — | 132.4 | — | — |
| 480 | Sodium (mEq/L) | 137.3 | 166.3 | 141.7 | 81.2 | 135.3 | 139.3 | 43.5 |
| 0 | Bicarbonate (mEq/L) | — | — | 23.2 | — | 23.1 | — | — |
| 480 | Bicarbonate (mEq/L) | — | — | — | — | 10 | — | — |

TABLE 6

Summary Cartridge 1

| Time (Min.) | | Cartridge | | Gain/Loss 4-liter Bag | 15-Liter | | Gain/Loss 15-Liter Bag |
| --- | --- | --- | --- | --- | --- | --- | --- |
| | | In | Out | 4-Liter Bag | (mEq) | In | Out | (mEq) |
| 0 | pH | — | — | 6.99 | — | 7.49 | — | — |
| 480 | pH | 6.9 | 7.09 | 7.06 | — | 6.9 | 6.997 | — |
| 0 | Sodium (mEq/L) | — | — | 124.4 | — | 137 | — | — |
| 480 | Sodium (mEq/L) | 135.4 | 142.6 | 139.9 | 62 | 133.2 | 137.2 | 57 |
| 0 | Bicarbonate (mEq/L) | — | — | 22 | — | 23.4 | — | — |
| 480 | Bicarbonate (mEq/L) | 28.4 | 31.8 | 31.1 | 36.4 | 24.9 | 26.4 | 22.5 |

TABLE 7

Summary Cartridge II

| Time (Min.) | | Cartridge | | Gain/Loss 4-liter Bag | 15-Liter | | Gain/Loss 15-Liter Bag |
| --- | --- | --- | --- | --- | --- | --- | --- |
| | | In | Out | 4-Liter Bag | (mEq) | In | Out | (mEq) |
| 0 | pH | — | — | 7.08 | — | 7.42 | — | — |
| 480 | pH | 7.106 | 7.235 | 7.2 | — | 7.036 | 7.122 | — |
| 0 | Sodium (mEq/L) | — | — | 126 | — | 136.60 | — | — |
| 480 | Sodium (mEq/L) | 132.6 | 139.9 | 135.3 | 37.2 | 130.1 | 133.7 | 99 |
| 0 | Bicarbonate (mEq/L) | — | — | 22 | — | 23.5 | — | — |
| 480 | Bicarbonate (mEq/L) | 26.2 | 28 | 26.9 | 19.6 | 22.5 | 24 | −15 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A cartridge for use in a dialysis system for removing toxins comprising:
a body having an inlet end and an outlet end;
an interior including at least four layers, the layers including a first layer of a resin selected from the group consisting of zirconium phosphate having a pH of approximately 2.5 to about 5 and urease, a second layer of a resin selected from the group consisting of zirconium oxide having a pH of approximately 9 to about 13 and urease, a third layer of zirconium phosphate, and a fourth layer of zirconium oxide having a pH of approximately 6.5 to about 7.5; wherein the first layer is different from the second layer; and
the interior being so constructed and arranged that a fluid entering the interior from the inlet end flows through the first layer, then the second layer, then the third layer, and then the fourth layer.

2. The cartridge of claim 1 wherein the zirconium oxide has been modified to remove a nitrate ion and substitute a bicarbonate ion therefor.

3. The cartridge of claim 1 wherein the zirconium oxide is in hydroxyl form.

4. The cartridge of claim 1 including a carbon layer located in juxtaposition to the outlet.

5. The cartridge of claim 1 wherein the first layer comprises approximately 200 to about 800 grams of zirconium phosphate.

6. A method for providing dialysis, the method comprising passing a dialysis fluid through a body having an inlet and an outlet and defining an interior, the interior including at least four layers, a first layer comprising either zirconium phosphate having a pH of approximately 2.5 to about 5 or urease, a second layer comprising either zirconium oxide having a pH of approximately 9 to about 13 or urease, a third layer comprising zirconium phosphate and a fourth layer comprising zirconium oxide having a pH of approximately 6.8 to about 7.5; wherein the first layer is different from the second layer.

7. The method of claim 6 wherein the dialysis fluid passing through the body contacts the fourth layer before contacting the first layer, the second layer and the third layer.

8. The method of claim 6 wherein the body includes two separate layers of zirconium oxide.

9. The method of claim 6 wherein the zirconium oxide is in bicarbonate form.

10. The method of claim 6 wherein the zirconium oxide is in hydroxyl form.

11. The method of claim 6 wherein the body includes a carbon layer positioned in juxtaposition to the outlet.

12. The method of claim 6 wherein the first layer comprises approximately 200 to about 800 grams of zirconium phosphate.

13. The method of claim 6 wherein the fourth layer comprises approximately 50 to about 200 grams of carbon.

14. A method of providing regenerative dialysis, the method comprising the step-ef removing at least some uremic toxins by passing a dialysis fluid through a body having an inlet and an outlet and defining an interior, the interior including at least four layers, a first layer comprising either zirconium phosphate having a pH of approximately 2.5 to about 5 or urease, a second layer comprising either zirconium oxide having a pH of approximately 9 to about 13 or urease, a third layer comprising zirconium phosphate and a fourth layer comprising zirconium oxide having a pH of approximately 6.8 to about 7.5; wherein the first layer is different from the second layer.

15. The method of claim 14 wherein the pH of the dialysis fluid as it exits the body is approximately 7.4.

16. The method of claim 14 wherein the pH of the dialysis fluid prior to entering the body is acidic.

17. The method of claim 14 wherein the pH of the dialysis fluid prior to entering the body is basic.

18. A device for regenerating a dialysis solution comprising:
a body including a resin bed, the resin bed including at least a layer of urease, zirconium phosphate, zirconium oxide, and carbon and being so constructed and arranged that a dialysis solution having a pH that is either basic or acidic entering the resin bed will exit the resin bed at a pH of approximately 7 to about 7.8, wherein a fourth layer of the resin bed contacted by the dialysis solution is zirconium oxide having a pH of approximately 6.8 to about 7.5.

19. A device for treating a patient with a dialysis solution comprising:
a body defining an interior and including an inlet, an outlet, and a resin bed comprising a layer of urease, a layer of zirconium oxide, and a layer of zirconium phosphate, wherein the inlet is in fluid communication with a source of basic or acidic dialysis solution and the resin bed is oriented so that a first layer of the resin bed that the dialysis solution contacts is either the urease layer or the zirconium phosphate layer and the zirconium oxide layer is so constructed and arranged that the dialysis solution entering the inlet will pass through the resin bed and exit the outlet with a physiologically acceptable pH, wherein the zirconium phosphate has a pH of approximately 2.0 to about 5.

20. A device for treating a patient with a dialysis solution comprising:
a body defining an interior and including an inlet, an outlet, and a resin bed comprising a layer of urease, a layer of zirconium oxide, and a layer of zirconium phosphate, wherein the inlet is in fluid communication with a source of basic or acidic dialysis solution and the resin bed is oriented so that a first layer of the resin bed that the dialysis solution contacts is either the urease layer or the zirconium phosphate layer and the zirconium oxide layer is so constructed and arranged that the dialysis solution entering the inlet will pass through the resin bed and exit the outlet with a physiologically acceptable pH, wherein the zirconium oxide layer has a pH of approximately 6.8 to about 7.5.

21. A method for constructing a cartridge for use in a system for providing dialysis, the method comprising:
providing a resin bed including a zirconium oxide layer and a zirconium phosphate layer; and
selecting and orienting the layers of zirconium oxide and zirconium phosphate to allow the resin bed to remove uremic toxins present in a dialysis solution entering the resin bed and causing the dialysis solution exiting the cartridge to have a physiological pH and a physiological acceptable electrolyte balance, wherein the zirconium phosphate layer has a pH of approximately 2 to about 8.

22. A method for constructing a cartridge for use in a system for providing dialysis, the method comprising:
providing a resin bed including a zirconium oxide layer and a zirconium phosphate layer; and
selecting and orienting the layers of zirconium oxide and zirconium phosphate to allow the resin bed to remove uremic toxins present in a dialysis solution entering the resin bed and causing the dialysis solution exiting the cartridge to have a physiological pH and a physiological acceptable electrolyte balance, wherein the zirconium oxide layer has a pH of approximately 6 to about 13.

* * * * *

UNITED STATES PATENT AND TRADEMARK OFFICE
CERTIFICATE OF CORRECTION

| | | |
|---|---|---|
| PATENT NO. | : 8,066,658 B2 | Page 1 of 1 |
| APPLICATION NO. | : 12/465214 | |
| DATED | : November 29, 2011 | |
| INVENTOR(S) | : Karoor et al. | |

It is certified that error appears in the above-identified patent and that said Letters Patent is hereby corrected as shown below:

In Claim 14, Column 23, Line 4, please delete "the step-ef".

Signed and Sealed this
Twenty-third Day of October, 2012

David J. Kappos
*Director of the United States Patent and Trademark Office*